(12) United States Patent
Garaczi et al.

(10) Patent No.: US 8,815,526 B2
(45) Date of Patent: Aug. 26, 2014

(54) METHODS AND REAGENTS FOR IDENTIFYING/ISOLATING T REGULATORY (TREG) CELLS AND FOR TREATING INDIVIDUALS

(75) Inventors: Edina Garaczi, Lakewood, OH (US); Hideaki Sugiyama, Yamanashi (JP); Rolland Gyulai, Szeged (HU); Kevin D. Cooper, Moreland Hills, OH (US); Thomas S. McCormick, Orange Village, OH (US)

(73) Assignee: Case Western Reserve University, Cleveland, OH (US)

(*) Notice: Subject to any disclaimer, the term of this patent is extended or adjusted under 35 U.S.C. 154(b) by 1427 days.

(21) Appl. No.: 11/910,442

(22) PCT Filed: Mar. 31, 2006

(86) PCT No.: PCT/IB2006/050992
§ 371 (c)(1),
(2), (4) Date: Jun. 20, 2008

(87) PCT Pub. No.: WO2006/103639
PCT Pub. Date: Oct. 5, 2006

(65) Prior Publication Data
US 2008/0279834 A1    Nov. 13, 2008

Related U.S. Application Data

(60) Provisional application No. 60/666,893, filed on Mar. 31, 2005.

(51) Int. Cl.
*G01N 33/50* (2006.01)
*G01N 33/53* (2006.01)
*C12Q 1/02* (2006.01)
*C12Q 1/24* (2006.01)

(52) U.S. Cl.
USPC ............... 435/7.24; 435/4; 435/7.1; 435/7.21

(58) Field of Classification Search
CPC .... C07K 116/28; C07K 14/435; G01N 33/53; G01N 2500/10; G01N 33/5047; G01N 33/505; G01N 33/5094; G01N 33/582; C12N 5/0637; C12N 5/0636; A61K 35/17; C12Q 1/02; C12Q 1/04
USPC ......................................... 435/4, 7, 7.1, 7.24
See application file for complete search history.

(56) References Cited

U.S. PATENT DOCUMENTS

2003/0049696 A1 *  3/2003  Norment et al. ............. 435/7.21

FOREIGN PATENT DOCUMENTS

WO       2007/113301 A1      10/2007

OTHER PUBLICATIONS

Garaczi et al. Glycoprotein A repetition predominant: a novel marker of human CD4+/CD25high+ regulatory T cells. J. Investigative Dermatology. vol. 124, Issue S4:A117. Apr. 2005.*
Marc Gavin and Alexander Rudensky; Control of immune homeostasis by naturally arising regulatory CD4+ T cells; Current Opinion in Immunology; 15:690-696; 2003.
Vincent Ollendorff, Tetsuro Noguchi, Odile Delapeyriere, and Daniel Birnbaum; The GARP Gene Encodes a New Member of the Family of Leucine-rich Repeat-containing Proteins; Cell Growth & Differentiation; vol. 5, 213-219; Feb. 1994.

* cited by examiner

*Primary Examiner* — Taeyoon Kim
(74) *Attorney, Agent, or Firm* — Hahn Loeser & Parks LLP

(57) ABSTRACT

An affinity ligand is reactive to the GARP protein may be capable of binding to an extracellular domain of GARP protein expressed on regulatory T (Treg) cells. The affinity ligand may be an antibody and may be used to identify Treg cells. A method comprises providing a blood sample from a subject and determining the amount of Treg cells in that sample. A composition containing Treg cells may be administered to an individual to suppress effector T cell activity in the individual. A composition containing an affinity ligand capable of binding to a GARP domain may be administered to an individual to suppress Treg cell activity and increase effector T cell activity in the individual. A kit for detecting Treg cells may include an affinity ligand reactive with mammalian GARP protein.

16 Claims, 13 Drawing Sheets

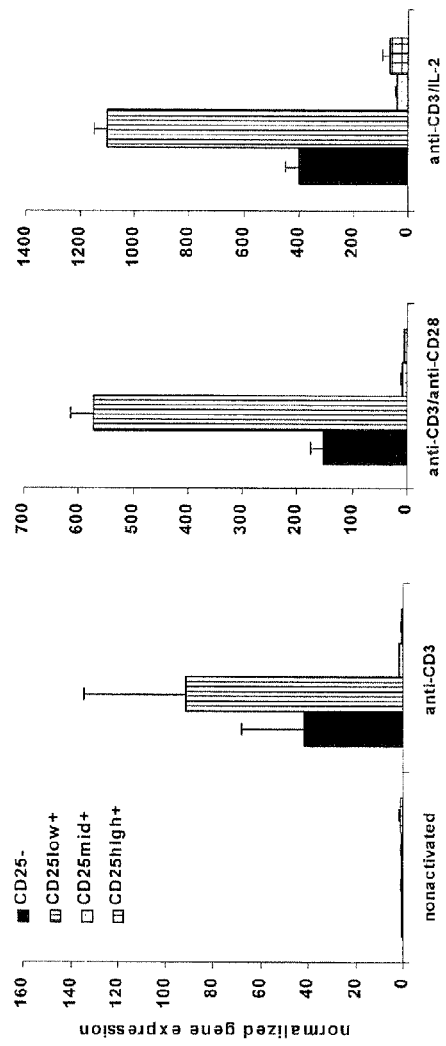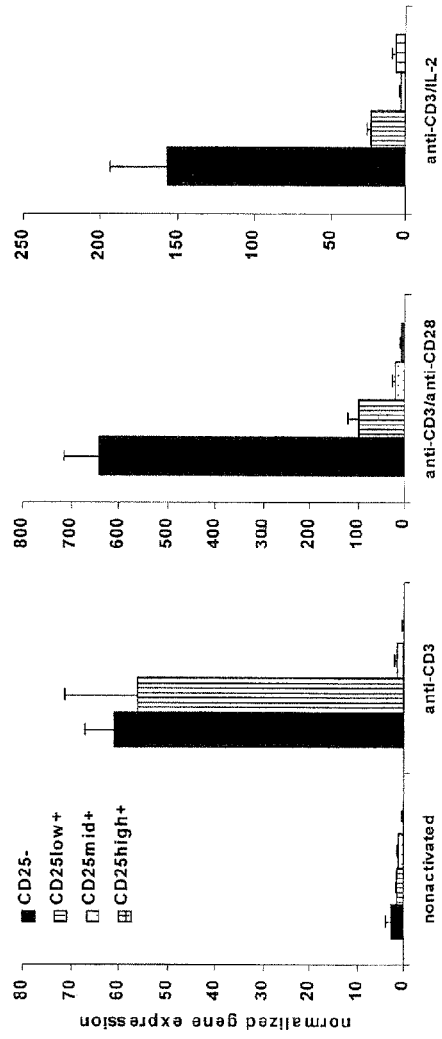
Figure 9

*Severity Index (SI)*

METHODS AND REAGENTS FOR IDENTIFYING/ISOLATING T REGULATORY (TREG) CELLS AND FOR TREATING INDIVIDUALS

BACKGROUND OF THE INVENTION

Naturally occurring regulatory T cells (Treg) are critical for maintaining a balance between beneficial and harmful autoreactive T cell responses. Treg cells (formerly called suppressor T cells) generally are responsible for controlling autoreactive T cell responses in a variety of immune responses. The existence of sub-populations of T cells that specialize in the suppression of immune responses was previously speculated in the early 1970s. Following these observations, "suppressor T cells" were found to be depressed in psoriasis and atopic dermatitis. It has been previously demonstrated, using allogeneic mixed lymphocyte reactivity (Allo-MLR) reactions, that T cells isolated from peripheral blood mononuclear cells (PBMC) of patients with psoriasis were less efficient at suppressing an MLR reaction than non-psoriatic suppressors. However, as with many early suppressor T cell studies, there was no further investigation of the role of suppressor T cells in psoriasis or dermatitis.

Recently, suppressor T cells have re-emerged as regulatory T cells (Treg) because a distinct phenotype was identified. Several recent reviews have described the re-emerging idea of T cells that regulate self-reactive T cells to maintain peripheral tolerance (non-autoimmune recognition of organ antigens). The identification of this class of Treg cell in human peripheral blood has also re-energized the field to concentrate on the potential mechanism(s) of action of this class of cell. Impaired capacity or removal of Treg cells allows excessive proliferative responses of pathogenic T cells.

Several subsets of Treg cells have been described and much progress has been made in understanding their ontogeny, function, and mechanisms of action. One such subset is the naturally occurring CD4(+)CD25(+) Treg that arise in the thymus and express the transcription factor Foxp3. However, Treg can also be induced in the periphery after immune activation. One such subset of Treg cells produce immunoregulatory cytokines, such as Interleukin-10 (IL-10) and are referred to as Tr1 cells. Regulatory T cells have also been classified as CD8+ Treg and TGF-β producing cells (Th3 cells), and exert their suppressive functions at least in part via the effects of these cytokines. The historical background and the spectrum of these T cell populations to which regulatory functions have been attributed, are well known in the art.

CD4+ cells that constitutively express the Interleukin-2 receptor (IL-2R) α-chain (CD25) have been identified as Treg cells in mice. This population was initially identified by its ability to inhibit the development of autoimmune gastritis that develops following neonatal thymectomy, and is capable of being enriched within the 10% of peripheral CD4+ cells that express CD25. CD4+CD25+ Treg cells also show a remarkable suppressive capacity both in vitro and in vivo. Transfer of these Treg cells reduces the pathology of experimentally induced autoimmune diseases such as gastritis, insulin-dependent diabetes mellitus, and colitis, whereas depletion of CD4+CD25+ Treg cells results in the development of systemic autoimmune diseases.

Treg cell function is a critical determinant of recrudescence in infections with intracellular microbes, in chronic inflammatory diseases, and in cancers. Thus, the natural presence of Treg cells in the immune system makes them a good target to manipulate and control pathologic as well as physiologic immune responses. However, strategic manipulation of Treg cells requires appropriate cell surface markers to distinguish them from non-regulatory T cells.

Treg cells are identifiable as CD4+ T cells that express relatively high levels of CD25. However, since activated T cells also generally express CD25, CD25 expression is normally not specific to Treg cells. It is known that expression of forkhead/winged-helix transcription factor FOXP3 differentiates Treg cells from activated T cells. FOXP3 is a member of a large family of transcription factors that drive numerous cellular responses and is critical for the development of murine CD4+CD25+ Treg cells and its high expression helps validate Treg cell purification. Recently, Foxp3 was identified as the gene responsible for an autoimmune condition in mice termed "scurfy", where mutation results in lethality 15-20 days following birth, induced by multi-organ infiltration of over-proliferating CD4+ T cells. Foxp3 knockout mice (Foxp3$^{-/-}$) exhibit lymphoproliferative disorders of the same magnitude as scurfy mice. Interestingly, adoptive transfer of wildtype lymphocytes protected the scurfy mice from developing disease. It was also observed, that the knockout Foxp3 mice do not possess a regulatory T cell (CD4+CD25+) population, in contrast to their wildtype counterparts, and, as with the scurfy animals, Foxp3$^{-/-}$ mice were protected by adoptive transfer of wildtype lymphocytes. The gene is highly conserved in humans and rodents, and mutations within FOXP3 result in a severe human autoimmune syndrome referred to as IPEX (immune dysregulation, polyendocrinopathy, enteropathy, X-linked syndrome). However the protein product of the FOXP3 gene, scurfin, is intracellularly expressed, and thus has limited utility for manipulation of viable cells.

Currently, CD25 expression is considered to be the most suitable cell surface marker for regulatory T cells, representing 5-10% of CD4+ T cells in normal naive mice. It is unknown, however, what percentage of CD25+ cells are regulatory T cells within the human CD4+ subset, because CD25 is upregulated on activated for memory type T cells, as well. Without previous T cell receptor (TCR) stimulation, human CD25high+ cells express high levels of intracellular and low levels of cell surface CTLA-4 (CD152), and constitutively express CD122 (IL-2R beta chain), CD45RO, HLA-DR, CD62L and CD71 in the physiologic state that is commonly used to identify naturally occurring Treg cells. However, these cell surface receptors are also upregulated on activated non-regulatory T cells. While regulatory T cell function in mice has been well described, revealing the identity and function of their human counterparts has been controversial because of a lack of specific markers to accurately identify this subset. Therefore, there is a need for identification of alternative markers for CD25high+ Treg cells to facilitate the progress of research in naturally occurring human regulatory T cells. Recently, it was disclosed that regulatory T cells may be identified by consistent lack of expression of the IL-7R (CD127) which in combination may mark Treg cells more specifically than CD4CD25 staining. However, this selection process will not allow for the direct selection of Treg cells.

Murine CD4+CD25+ Treg cells are anergic (have a depressed response to antigens or are non-responsive to antigens) when stimulated in vitro with anti-CD3 mAbs, but proliferate upon addition of exogenous interleukin-2 (IL-2). After TCR-mediated stimulation, CD4+CD25+Treg cells suppress the activation and proliferation of other CD4 and CD8 T cells in antigen specific and antigen-nonspecific manners via a mechanism that requires cell—cell contact and, in most systems, is independent of production of immunosuppressive cytokines. Murine CD4+CD25+ Treg cells uniquely constitutively express cytoplasmic cytotoxic T lymphocyte-associated antigen (CTLA)-4, a receptor for the co-stimulatory ligands B7-1 and B7-2 and a negative regulator of T cell activation. Expression of this molecule may be required for these cells to suppress immune responses in vivo.

Leucine rich repeat containing (LRRC) proteins exhibit 20-29 leucine repeat motifs. These motifs are present in many proteins that participate in protein-protein interactions and exhibit various functions and are found in various cellular locations. LRRC 3D structural units consist of a beta strand (LxxLxLxxN/CxL conserved pattern) and an alpha helix. This results in a curved overall structure with parallel f3 sheets on the concave side, and helices on the convex side of the curve. This "finger-like" repeating structure's primary function is to provide a framework for protein-protein interaction. The "horseshoe" like shape of the LRRC facilitates these protein interactions. Several LRRC subfamilies have been identified, with the most recent consensus of seven distinct subgroups. LRRC 3D structures have been described and LRRC regions have been identified in numerous proteins including, ribonuclease inhibitors, proteoglycans, tyrosine kinase receptors and Toll like receptors. LRRC proteins are proposed to participate in biological activities, such as receptor hormone binding, cell adhesion, enzyme reactivity and cell trafficking. LRRC proteins have also been demonstrated to participate in neural development, apoptosis and regulation of gene expression. It is believed that in all of these interactions, LRRC domains facilitate protein-protein interaction.

BRIEF SUMMARY OF THE INVENTION

It is, therefore an aspect of the present invention to provide a method of screening cells for identity as Treg cells. It is also an aspect to provide a method of separating Treg cells from other types of cells. It is a further aspect of the invention to provide an antibody specifically reactive to Treg cells.

A relatively new member of the LRRC family was named glycoprotein A repetitions predominant (GARP), and classified as a leucine rich repeat containing protein (later named LRRC32). The protein, the human sequence of which is provided as SEQ. ID. NO. 1, is 662 amino acids long, beginning with a methionine and a hydrophobic amino acid region believed to constitute a signal peptide. The majority of the molecule is a putative extracellular region containing 22 leucine rich repeats. The 22 leucine rich repeat regions are extracellular and are located upstream of a putative membrane spanning region, amino acids 628-648 of SEQ. ID. NO. 1, and a potential cytoplasmic region, amino acids 649-662.

In general, the present invention provides an affinity ligand reactive with a GARP protein and a method of creating the same. The affinity ligand may be an antibody reactive with an extracellular domain of GARP, such as a polypeptide having the sequence of SEQ. ID. No. 1. Alternatively, the antibody may be reactive to a polypeptide comprising at least one sequence selected from SEQ. ID. NOS. 3-24. The method of producing such an affinity ligand includes methods of raising an antibody to a GARP protein or polypeptide thereof as described hereinbelow.

The present invention also provides a method for obtaining Treg cells by identifying T cells that express a GARP protein. The method may include contacting T cells with an affinity ligand as described above and isolating the Treg cells based at least in part on the binding of the affinity ligand to a portion of the GARP protein. Likewise, a kit for detecting Treg cells in a blood sample may contain an affinity ligand that is reactive with a mammalian GARP protein.

BRIEF DESCRIPTION OF THE DRAWINGS

In the accompanying drawings, which are incorporated in and constitute a part of the specification, embodiments of methods and reagents related to Treg cells are illustrated which, together with the detailed description given below, serve to describe the examples. It will be appreciated that the embodiments illustrated in the drawings are shown for the purpose of illustration and not for limitation. It will be appreciated that changes, modifications and deviations from the embodiments illustrated in the drawings may be made without departing from the spirit and scope of the invention, as disclosed below.

FIG. 2A shows flow cytometric gating of CD25high+, CD25mid+, CD25low+ and CD25− cells after staining with antibodies specific for CD4 and CD25. FIG. 2B shows expression of various cell surface markers on CD25high+, CD25mid+, CD25low+ and CD25− cells.

FIG. 9 shows an example of neither CD25high+ nor CD25mid+ cells expressing cytokines upon polyclonal stimulation. Expression of IL-10 (FIG. 9A) and IL-2 (FIG. 9B) were examined.

DETAILED DESCRIPTION OF THE INVENTION

Figure 1:
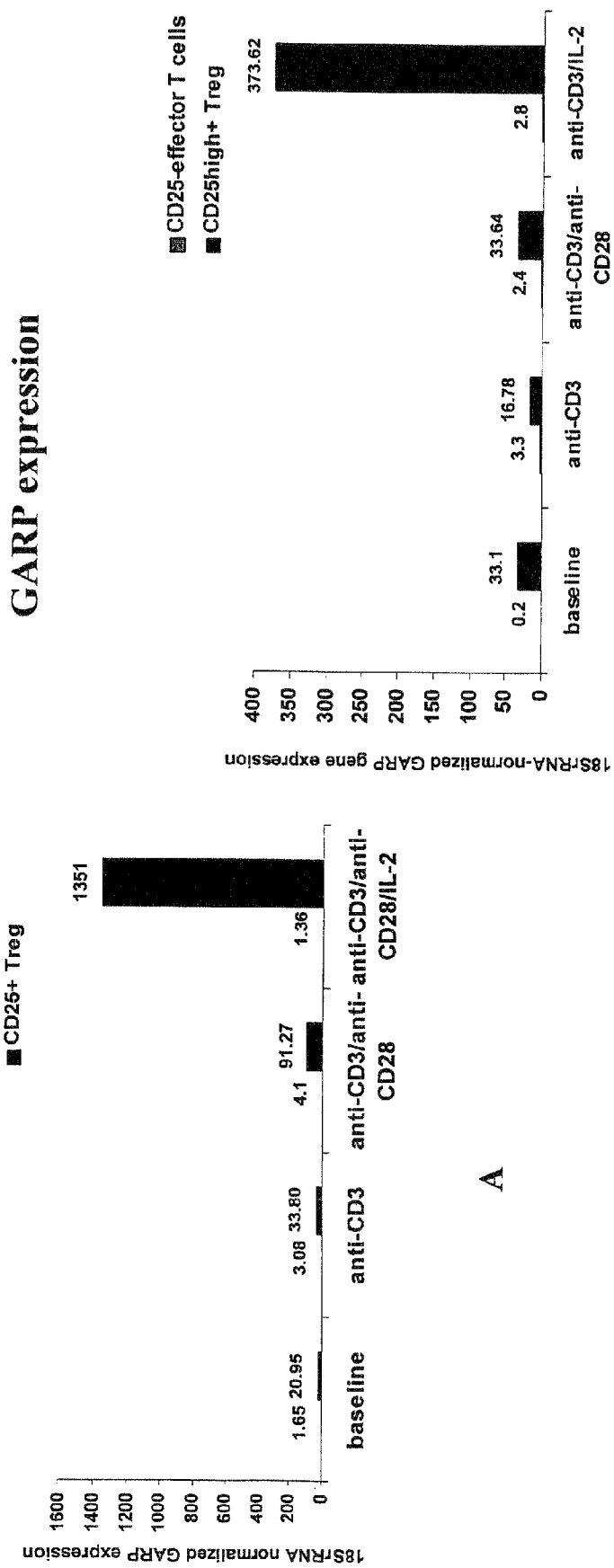
FIG. 1 illustrates example results of GARP mRNA expression in unstimulated and stimulated Treg (CD4+CD25+) and CD25− T cells. In panels A and B, cells were isolated by two different methods as described in the Detailed Description.

It has been discovered that human Treg cells express a gene encoding a transmembrane protein that is useful in distinguishing Treg cells from other cells, including activated T cells. This protein is called glycoprotein A repetitions predominant (GARP), also called D11S833E, also called LRRC32 (GenBank Gene ID 2615; Locus tag HGNC:4161; MIM: 137207). GARP encodes a type I transmembrane protein that contains 22 leucine-rich repeats.

Additionally, at least two types of Treg cells have been discovered. One Treg cell type may be CD4+ and may express relatively high levels of CD25. These cells, called CD25high+ cells, are efficient suppressor cells that generally are not capable of proliferation. They may represent about 1% of human CD4+ cells. Another Treg cell type may be CD4+ and may express levels of CD25 relatively lower than CD25high+ cells. These cells, called CD25mid+ cells, are less efficient suppressors of effector T cells than CD25high+ cells, but are capable of proliferation after polyclonal stimulation and, therefore, may be expanded in vitro. These cells are more effective inhibitors of IL-2 mRNA production following T cell stimulation. These cells may represent about 2-3% of human CD4+ cells.

Based on these findings, the following inventions are described.

In one example, methods for identifying, isolating and/or purifying Treg cells are described. One method generally includes identifying T cells or CD4+ T cells that express the GARP gene. In one embodiment, a GARP protein may be detected on the surface of the cells. An antibody specific for a region of the GARP protein detectable on the surface of intact cells may be used.

In another example, affinity ligands that bind to GARP are described. In one embodiment, the affinity ligand may be an antibody. In other embodiments, the affinity ligands may be immunoreactive fragments from antibodies, peptides, aptamers, and the like. The affinity ligands may bind to a region of GARP. The peptides may bind to a region of GARP that is detectable or available on the surface of Treg cells.

In other examples, various methods, such as for treating individuals, are described. One type of individual that may be treated may have, for example, hyperactive cellular immune activity. One type of individual like this may have an autoimmune disease, like psoriasis or multiple sclerosis, for example. An example method for treating an individual like this may involve administration of Treg cells to the individual for the purpose of suppressing or down-regulating effector T cell activity in the individual. The Treg cells may be administered locally or systemically. In one example, the Treg cells that are administered may be obtained from an individual using methods for isolating Treg cells described in this disclosure.

In another example, an individual that is treated may have cellular immune activity that is less than desirable or optimal. One example individual like this may be an individual that has a tumor or malignancy that is not being acted upon or is being inefficiently acted upon by T effector cells in the individual. An example method for treating an individual like this may involve administration to the individual of a composition capable of binding Treg cells in the individual for the purpose of inactivating the endogenous Treg cells and increasing the function of effector T cells in the individual. One type of composition that may be administered to the individual may include one or more affinity ligands, like antibodies for example, that can bind to GARP that is detectable on the surface of Treg cells.

In another example, methods for identifying, diagnosing and/or monitoring cellular immune activity is described. One example method may involve measuring or quantifying Treg cells in an individual. The number of Treg cells may be used to infer a level of T effector cell activity in the individual. In one method, Treg cells in a specified volume of the blood of an individual may be quantified using an affinity ligand that binds to GARP protein.

In another example, methods for identifying or isolating Treg cells that efficiently suppress T effector cell activity (e.g., CD25high+ cells) and generally do not proliferate are described. One method like this may involve isolating CD4+, CD25high+ cells. In another example, methods for identifying or isolating Treg cells that are capable of suppressing T effector cell activity and are capable of proliferating and being expanded in vitro (e.g., CD25mid+ cells). One method like this may involve isolating CD4+, CD25mid+ cells. Generally, the CD25high+ cells express higher levels of GARP than do CD25mid+ cells.

GARP

Genes differentially expressed in Treg cells were sought using microarray studies. GARP was identified as a gene whose expression was increased in CD25+ T cells as compared to CD25- T cells. GARP encodes a leucine-rich repeat region (LRR) containing a type I transmembrane-spanning domain with an extracellular region comprised of LRR. The GenBank GeneID for this sequence is 2615 and is provided herein as SEQ. ID. NO. 2. Studies of GARP expression in Treg cells are described in the Examples section of this disclosure, below.

Affinity Ligands to GARP

Affinity ligands capable of binding to GARP protein may be of a variety of types. In one embodiment, the affinity ligands are antibodies. The antibodies may be polyclonal antibodies or monoclonal antibodies. The affinity ligands may also include immunoreactive fragments of antibodies, peptides, aptamers, and the like. In one embodiment, the affinity ligands bind to a region of the GARP protein that is extracellular or displayed on the surface of cells. Based on the structure of the GARP protein, it is believed that the extracellular domain of the protein includes leucine-rich repeats.

Affinity ligands, like antibodies, may be made in a variety of ways. In one example, an antibody specific for GARP is made by using all or part of the GARP protein as an antigen. The GARP protein may be purified from cells. The entire purified GARP protein may be used as an antigen. Peptides derived from the GARP protein may also be used as antigens. The peptides may be derived from the full length GARP protein, after digestion with proteases, for example. Peptides may also be synthesized, based on the known amino acid sequence of the GARP protein. In one example, the peptides may be selected from one or more of the leucine rich repeat regions of the GARP protein provided as SEQ. ID. NOS. 3-24. In the sequences provided, SEQ. ID. NO. 3 corresponds to amino acids 8-31 of SEQ. ID. NO. 1; SEQ. ID. NO. 4 corresponds to amino acids 48-71 of SEQ. ID. NO. 1; SEQ.

ID. NO. 5 corresponds to amino acids 72-95 of SEQ. ID. NO. 1; SEQ. ID. NO. 6 corresponds to amino acids 97-122 of SEQ. ID. NO. 1; SEQ. ID. NO. 7 corresponds to amino acids 123-147 of SEQ. ID. NO. 1; SEQ. ID. NO. 8 corresponds to amino acids 148-171 of SEQ. ID. NO. 1; SEQ. ID. NO. 9 corresponds to amino acids 172-195 of SEQ. ID. NO. 1; SEQ. ID. NO. 10 corresponds to amino acids 197-217 of SEQ. ID. NO. 1; SEQ. ID. NO. 11 corresponds to amino acids 218-240 of SEQ. ID. NO. 1; SEQ. ID. NO. 12 corresponds to amino acids 242-264 of SEQ. ID. NO. 1; SEQ. ID. NO. 13 corresponds to amino acids 265-286 of SEQ. ID. NO. 1; SEQ. ID. NO. 14 corresponds to amino acids 314-337 of SEQ. ID. NO. 1; SEQ. ID. NO. 15 corresponds to amino acids 339-361 of SEQ. ID. NO. 1; SEQ. ID. NO. 16 corresponds to amino acids 362-385 of SEQ. ID. NO. 1; SEQ. ID. NO. 17 corresponds to amino acids 386-409 of SEQ. ID. NO. 1; SEQ. ID. NO. 18 corresponds to amino acids 410-432 of SEQ. ID. NO. 1; SEQ. ID. NO. 19 corresponds to amino acids 442-465 of SEQ. ID. NO. 1; SEQ. ID. NO. 20 corresponds to amino acids 467-488 of SEQ. ID. NO. 1; SEQ. ID. NO. 21 corresponds to amino acids 490-512 of SEQ. ID. NO. 1; SEQ. ID. NO. 22 corresponds to amino acids 514-538 of SEQ. ID. NO. 1; SEQ. ID. NO. 23 corresponds to amino acids 540-558 of SEQ. ID. NO. 1; and SEQ. ID. NO. 24 corresponds to amino acids 560-583 of SEQ. ID. NO. 1.

Anti-GARP antibodies may be polyclonal or monoclonal antibodies. Polyclonal antibodies may be raised against GARP protein by injecting the GARP protein, with or without one or more adjuvants known in the art, into an animal in which the antibodies will be raised. Suitable animals for the generation of antibodies include rabbits, chicken, mice, rats, sheep, goats, and guinea pigs, for example. Typically, the animal may be injected with the antigen more than once. The antibody will typically be isolated from a blood sample from the animal, although in the case of chicken, antibody may be purified from egg yolk.

Antibodies may also be raised against GARP protein using a genetic immunization technique, as offered by different commercial services. In such a technique, the antibody is raised without the purification of the protein but instead is raised by inserting an antigen-encoding gene directly into cells of the host animal. Methods for genetic immunization include intradermal or intramuscular injection with a needle or gene gun shooting. The gene gun technique involves the shooting of gold particles (1-2 µm average diameter) coated with antigen-encoding DNA into the skin cells of the animal. The DNA is then expressed in the cells and the antigen is thereby presented to the immune system. The DNA may also include coding sequences for one or more adjuvants to stimulate antibody production in the animal. The DNA may be a vector that includes sequences that ensure and enhance expression of the antigen-encoding gene. Examples of such sequences include the cytomegalovirus (CMV) promoter and human growth hormone terminator. The vector may also contain marker elements such as the firefly luciferase gene or other similar reporter genes that allow for determination of transformation of cells with the DNA. The vector may be a linear expression element which contains three elements, a promoter, a gene and a terminator, that may be joined by a polymerase chain reaction (PCR).

In one gene immunization technique, the antigen encoding sequence may be derived by standard techniques such as PCR amplification and/or restriction endonuclease digestion of an isolated sequence followed by insertion and ligation into the vector. The DNA may then be used to coat a gold particle, which is then injected into skin cells using a gene gun. The pressure used to inject the skin cells is typically optimized for maximum penetration to reach dendritic cells in the epidermis. Alternatively, the DNA may be injected intramuscularly or subcutaneously. Injection techniques generally require a greater amount of DNA than the gene gun technique to achieve similar immune responses.

In one example, peptides spanning the length of the GARP protein are synthesized. In another example, peptides are synthesized that include only a portion of the GARP protein. For example, a peptide may contain the amino acid sequence of one or more of the LRR sequences mentioned above. The peptides are then used as antigens to obtain peptide antibodies. The peptides may be used as part of an immunogen, in rabbits for example, and antisera containing antibodies specific for the peptide may then be obtained from the animal. The peptides may be used as part of an immunogen, in mice for example, and spleen cells from the mice may then be used to produce hybridoma cells secreting antibodies specific for the peptides. The antibodies obtained may be tested to determine if they can bind to GARP. In one example, the antibodies are tested to determine if they bind to an extracellular region of GARP that is displayed on the surface of Treg cells.

Methods for Identifying Treg Cells

A variety of methods may be used to identify and/or isolate Treg cells. In one example method, an affinity ligand capable of binding to GARP protein may be used. The affinity ligand may be capable of binding to an extracellular region of GARP. The affinity ligand may be used to contact a mixture of cells that includes Treg cells. Detection of affinity ligand bound to GARP may then be used to identify and/or isolate Treg cells from the mixture. A variety of methods using affinity ligands to identify and/or isolate cells are known in the art. In one example, flow cytometric cell sorting may be used. Other methods using magnetic beads, columns, and the like may also be used.

In one example, PBMCs are contacted with a fluorescently-labeled anti-GARP antibody reactive with a GARP epitope available on the cell surface. Treg cells are then flow sorted based, at least in part, on fluorescence due to the cell surface-bound antibody.

In one example, Treg cells expressing relatively very high levels/of GARP may be isolated. These cells may be called GARPhigh+ cells and have properties similar to CD25high+ cells. The GARPhigh+ cells may efficiently suppress T effector cell activity and may not be capable of being stimulated to proliferate. In another example, Treg cells expressing levels of GARP generally lower than GARPhigh+ cells may be isolated. These cells may be called GARPmid+ cells and may have properties similar to CD25mid+ cells. The GARPmid+ cells may have the capability of being stimulated to proliferate.

It is envisioned that isolated Treg cells may have a variety of uses. The isolated cells may be used in scientific studies. The isolated cells may be used in diagnostic studies. One type of diagnostic study may include examination of the functional activity of these cells. Examination of functional activity may be performed in a variety of ways. One way, for example, may be to test the ability of Treg cells to suppress the activity of effector T cells. Assays where Treg cells are mixed with effector T cells, like mixed lymphocyte reactions, may be used. The isolated cells may also be used therapeutically by introduction of the cells into an individual.

Methods for Detecting Treg Cells and Diagnosing/Monitoring Abnormal Conditions

Methods for detecting Treg cells in, for example, the blood of an individual may be used. Detection of Treg cells in the blood may provide information on the level of effector T cell activity in an individual. In one example, blood may be drawn from an individual having or suspected of having an autoimmune disease. The number of Treg cells in a sample from the blood may be determined for the purpose of diagnosing or following the course of an autoimmune disease. In one example, a number of Treg cells that is less than expected may indicate presence or flaring of an autoimmune disease. In another example, a blood sample may be drawn from an individual having a malignancy, or a sample of tissue may be taken from or around a malignancy in an individual. The number of Treg cells in the sample may be determined for the purpose of inferring a cellular immune activity against the malignancy in the individual.

Methods for Treating an Individual by Administering a Composition Containing an Affinity Ligand Reactive to GARP Administration to an individual of a composition containing an affinity ligand specific for GARP protein may be used. The affinity ligands generally may be administered to an individual for the purpose of binding to and suppressing the activity of Treg cells in an individual. This suppression generally provides for increased activity of effector T cells in the individual. In one instance, an individual receiving administration of affinity ligands specific for GARP may have a tumor or malignancy, the spread or progression of which is thought to be decreased by increase of effector T cell activity in the individual.

Administration of the compositions that contain the affinity ligands may be performed in a variety of ways. For example, the compositions may be administered locally or systemically. For example, the compositions may be administered parenterally or by other routes.

Methods for Treating an Individual by Administering Treg Cells to the Individual Administration to an individual of a composition containing functional Treg cells may be used. The Treg cells may be administered to an individual for the purpose of increasing suppressor T cell activity in the individual. In one instance, an individual receiving administration of Treg cells may have an autoimmune condition. The Treg cells may be administered for the purpose of suppressing autoimmune activity in the individual.

Administration of compositions containing Treg cells may be performed in a variety of ways. For example, the compositions may be administered locally or systemically. For example, the compositions may be administered parenterally or by other routes.

EXAMPLES

The examples are for the purpose of illustrating an embodiment and is not to be construed as a limitation.

Example 1

Identification of GARP Expression in Treg Cells

DNA microarray technology was used to compare patterns or gene expression in freshly isolated and stimulated CD25+ and CD25− cells.

To isolate cells, human peripheral blood mononuclear cells (PBMCs) were isolated from heparinized venous blood by Histopaque (Sigma-Aldrich, St. Louis, Mo.) density gradient centrifugation according to the manufacturer's directions. The cells were incubated for 30 min. with anti-CD4-FITC (BD Pharmingen, San Diego, Calif.) and anti-CD25-APC (Caltag, Burlingame, Calif.) antibodies in the culture medium (RPMI 1640 medium supplemented with 10% FBS (Cambrex Bioproducts, Walkersville, Md.), L-glutamine, penicillin, streptomycin, (all from Cellgro Mediatech Inc., Herndon, Va.) 2 Mercapto-ethanol (Sigma-Aldrich). Control PBMCs were stained with the appropriate isotype antibodies (BD Pharmingen). The cells were washed high speed flow-sorted according to their forward and side scatter properties, excluding large activated cells using a BD FACSAria. Confirmation that the sorted cells were Treg cells was made by demonstration of FOXP3 expression in cells. The sorted normal human CD25+ cells were stimulated using anti-CD3 and anti-CD-28 antibodies. mRNA was then isolated from the cells and used to synthesize cRNA. The cRNA was used to probe microarrays. GARP was identified as a gene whose expression was upregulated in the TCR-stimulated CD25+ cells.

Example 2

Detection of GARP Expression in Unstimulated and Stimulated Treg and CD25− T Cells Starting with PBMCs, CD4+ T cells were isolated by negative bead selection. From this CD4+ population, 3-4% of the CD4+CD25+ population was selected and sorted. These isolated cells represent the regulatory T cell population. The cells were rested overnight. The cells ($30 \times 10^3$/well) were then stimulated for 72 hours with plate-bound anti-CD3 (0.5 µg/ml) in the presence or absence of soluble anti-CD28 (1 µg/ml) and/or IL-2 (50 U/ml) in 200 ul final volume of culture medium in round-bottomed 96-well plates. Seventy-two hours following stimulation, the cells were lysed and total RNA was extracted using an RNeasy mini kit (Qiagen Inc., Valencia, Calif.).

The RNA was used in real-time quantitative RT-PCR. RNA was reverse transcribed using 200 U of Moloney-murine leukemia virus reverse transcriptase (MM-LV RT) (Invitrogen, Carlsbad, Calif.), according to the manufacturer's instructions. Q-RT-PCR was used to quantify the relative abundance of products of the genes using primers specific for GARP, FOXP3, IL-10, IL-2 or 18S ribosomal RNA (rRNA) and TaqMan Universal Master Mix in a 96-well microtiter plate format on an ABI PRISM 7700 Sequence Detection System (all primers were from PE Applied Biosystems, Foster City, Calif.). 18s specific primers and internal fluorescent TaqMan probe were designed as follows: 5'-CAT-TCT-TGG-CAA-ATG-CTT-TCG-3', 5'-CGC-CGC-TAG-AGG-TGA-AAT-TC-3' (from PE Applied Biosystems, Foster City, Calif.); 18S probe: VIC-ACC-GGC-GCA-AGA-CGG-ACC-AGA-TAMRA (Invitrogen, Carlsbad, Calif.). Each PCR reaction was performed in triplicate, using the following conditions: 2 min at 50° C. and 10 min at 95° C. followed by 40 cycles of 15 s at 95° C. and 1 min at 60° C. Normalized gene expression was calculated using ACT method (quantity of target gene normalized to 18s ribosomal RNA) in each sample.

GARP mRNA was measured and normalized to 18S ribosomal RNA for both CD25+ and CD25− populations. Shown in FIG. 1A is the summary graph representing GARP mRNA expression in unstimulated, and stimulated conditions, indicating that GARP mRNA is present in CD25+ populations, both resting and stimulated at higher levels than represented in the non-CD25+ population of T cells.

In another study, a different method was used to obtain Treg cells. Using this method, bead selection as described above was eliminated. Instead, the isolated PBMC population was directly stained with anti-CD4 and anti-CD25 antibodies and sorted by flow cytometry. The top 1% of the CD4+CD25+ cells (CD25high+ cells; a more conservative estimate of regulatory T cells) were cultured directly into stimulatory conditions (described above). At 72 h post stimulation, total RNA was isolated from lysed cells (as above). Taqman PCR for GARP was performed using these samples, and the findings are summarized in FIG. 1B. Again, CD25high regulatory T cells exhibit much higher levels of GARP mRNA than CD25− cells, demonstrating that GARP expression is a marker for the regulatory T cell population in human PBMC.

Example 3

Comparison of Cell Surface Antigen Expression on CD25+ Cells

The phenotype and function of CD25high+ regulatory T cells was compared to CD25mid+, CD25low+ (1%, 2-3% and 18% of the total CD4+ population respectively) and CD25− populations. Normal human freshly isolated PBMCs were stained with anti-CD4-FITC, anti-CD25-APC or their isotype control antibodies. Positively stained CD4+ T cells were gated according to their forward and side scatter properties, excluding large activated cells. CD25high+, CD25mid+, CD25low+ and CD25− cells were high speed flow-sorted using the indicated sorting gates shown in FIG. 2A.

For phenotypic characterization of the CD25high+, CD25mid+, CD25low+ and CD25− cell subsets, the expression of various cell surface antigens on these cells was compared. Normal human PBMCs were stained with anti-CD3-PerCP, anti-CD4-APC, anti-CD25-PE, anti-CD62L-FITC, anti-CD45RO-FITC, anti-HLA-DR-FITC, anti-CD69-FITC, anti-CD71-FITC and anti-GITR-FITC or their isotype control antibodies and then fixed in 4% paraformaldehyde and analyzed by flow cytometry. Results are expressed as the mean±SEM (n=6) and are shown in FIG. 2B.

Figure 2:
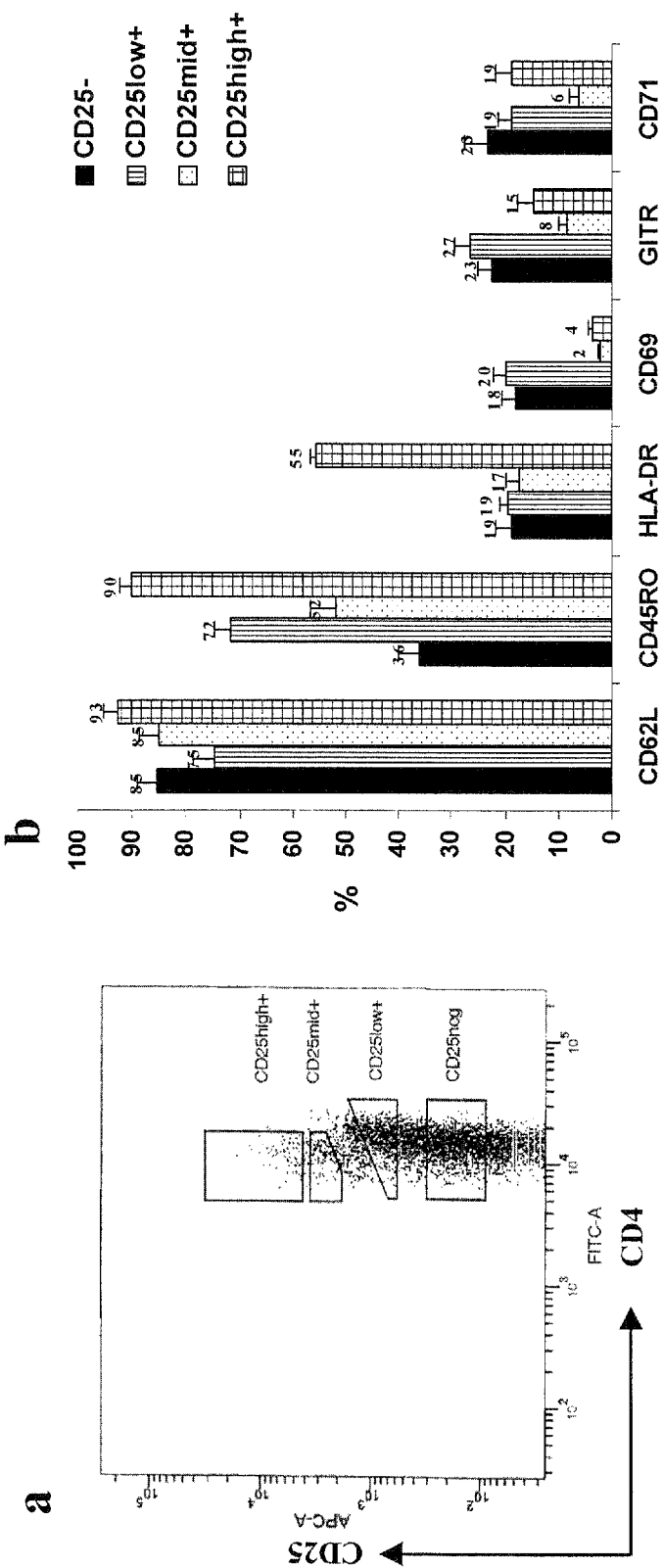
FIG. 2 illustrates an example of differential expression profiling of cell surface antigens on CD25high+ cells versus CD25mid+ cells.

The results in FIG. 2B showed that the lymph node homing receptor CD62L (L-selectin) was expressed on 94.8% of the CD25high+ and 89.2% of the CD25mid+ T cell subset. Also, 90% of CD25high+ cells expressed CD45RO compared to only 52% of the CD25mid+ cells indicating that CD25high+ cells represent a highly differentiated population. The expression of other surface markers associated with Treg cell profiles including HLA-DR, CD69, CD71, and GITR are also shown. There was higher expression of HLA-DR and CD71 on CD25high+ versus CD25mid+ T cells (p<0.001 and p=0.005 respectively), indicating distinct properties of these two populations. Low expression of CD69 on the CD25high+ and CD25mid+ populations indicates that they contain few activated T memory/effector cells.

Example 4

Comparison of GARP Expression to FOXP3 Expression

Expression levels of GARP (FIG. 3A) and FOXP3 (FIG. 3B) mRNAs were compared in simultaneously flow-sorted CD25high+, CD25mid+, CD25low+ and CD25− cells using quantitative real-time PCR.

The data showed that freshly isolated CD25high+ Treg cells expressed high levels of GARP and FOXP3 mRNAs (18SrRNA-normalized gene expression, mean±SEM: 44.42±3.5 and 71.11±8.0 respectively, n=4). These levels were 2-3 fold higher compared to CD25mid+ cells (18SrRNA-normalized gene expression, mean±SEM; GARP: 15.68±0.1 and FOXP3: 32.8±8.5, n=4). Both CD25low+ (18SrRNA-normalized gene expression, mean±SEM; GARP: 1.85±1.03 and FOXP3: 2.68±0.78, n=4) and CD25− cells (18SrRNA-normalized gene expression, mean±SEM; GARP: 0.33±0.09 and FOXP3: 0.33±0.05, n=4) expressed detectable levels of GARP and FOXP3 mRNAs. Thus, CD25high+ cells exhibit ~130 fold higher levels of GARP and ~210 fold higher levels of FOXP3 compared to CD25− cells, indicating that both genes are highly upregulated in resting Treg cells. Furthermore, CD25mid+ cells expressed moderate levels of GARP and FOXP3 mRNAs suggesting that this population may have significant regulatory function in vitro.

Example 5

Figure 4:
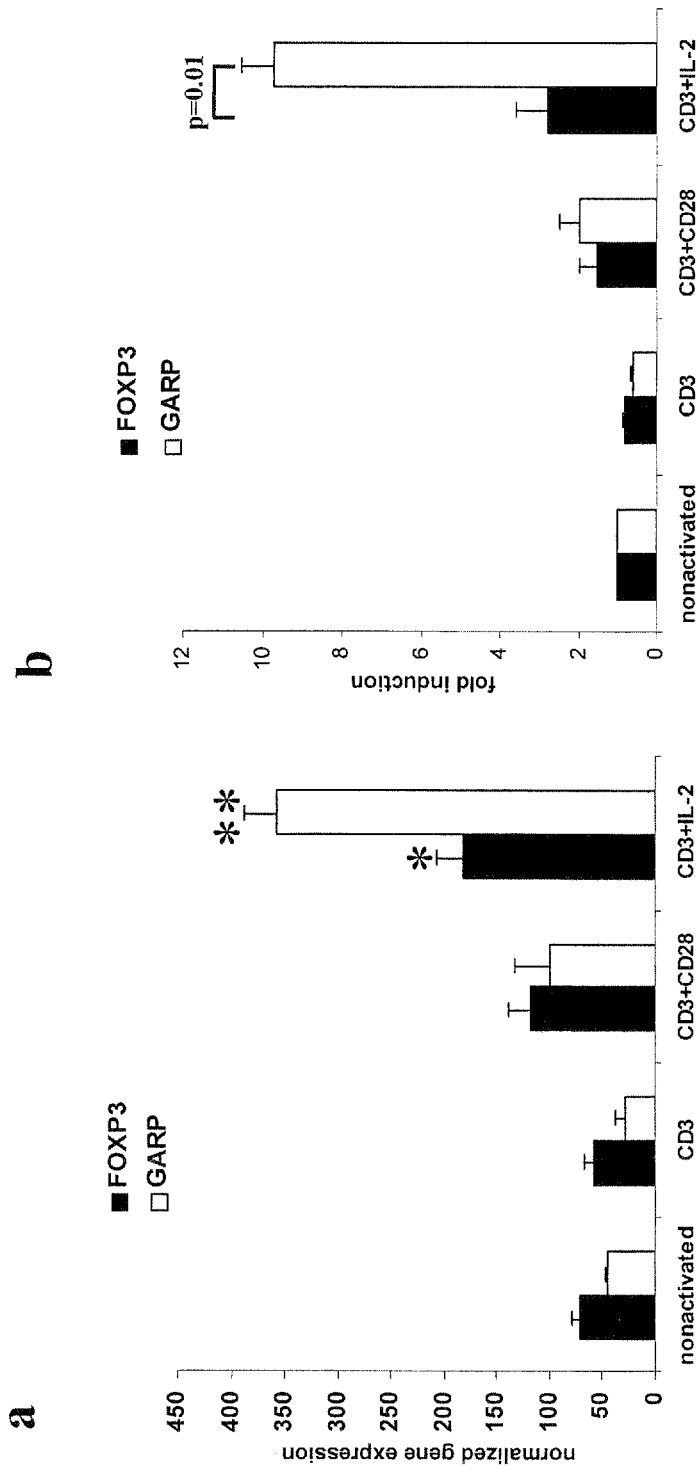
FIG. 4 illustrates an example showing that GARP is more sensitive for IL-2 dependent activation in CD25high+ T cells than FOXP3. Cells were activated with anti-CD3 in the presence or absence of anti-CD28 and or IL-2. 18SrRNA-normalized gene expression of GARP and FOXP3 mRNA was measured by quantitative RT-PCR (FIG. 4A). Fold induction was calculated from the normalized gene expression of activated versus non-activated cells (FIG. 4B). The data summarizes three independent experiments. Results are expressed as the mean±SEM. *p<0.05 compared to the FOXP3 expression in nonactivated cells, **p<0.01 compared to the GARP expression in nonactivated cells. Statistical analysis was performed using the Student's t test. P values<0.05 were considered significant.

Comparison of GARP with FOXP3 as a Marker for IL-2 Mediated Treg Cell Activation The normalized gene expression of GARP and FOXP3 was examined in CD25high+ cells following polyclonal stimulation in the presence or absence of exogenous IL-2 and soluble anti-CD28. CD25high+ cells were flow-sorted. The flow-sorted cells ($15 \times 10^3$/well) were stimulated with plate-bound anti-CD3 (0.5 µg/ml) (BD Pharmingen), in the presence or absence of soluble anti-CD28 (1 µg/ml) (BD Pharmingen) and/or exogenous IL-2 (50 U/ml) (R&D Systems), in round-bottomed 96-well plates (BD Pharmingen). All cells were cultured in a final volume of 200 µl of complete medium. After 72 h the cells were pulsed with 1 µCi/well [$^3$H]-thymidine for an additional 16 hours before harvesting; cpm/well was determined by scintillation counting (Beckman LS 6000SC, Beckman Coulter, Inc., Fullerton, Calif.). RNA was extracted and measured by quantitative RT-PCR. 18SrRNA-normalized gene expression of GARP and FOXP3 mRNA was measured by quantitative RT-PCR. The results are shown in FIG. 4A. In FIG. 4B, fold induction was calculated from the normalized gene expression of activated versus non-activated cells.

Figure 3:
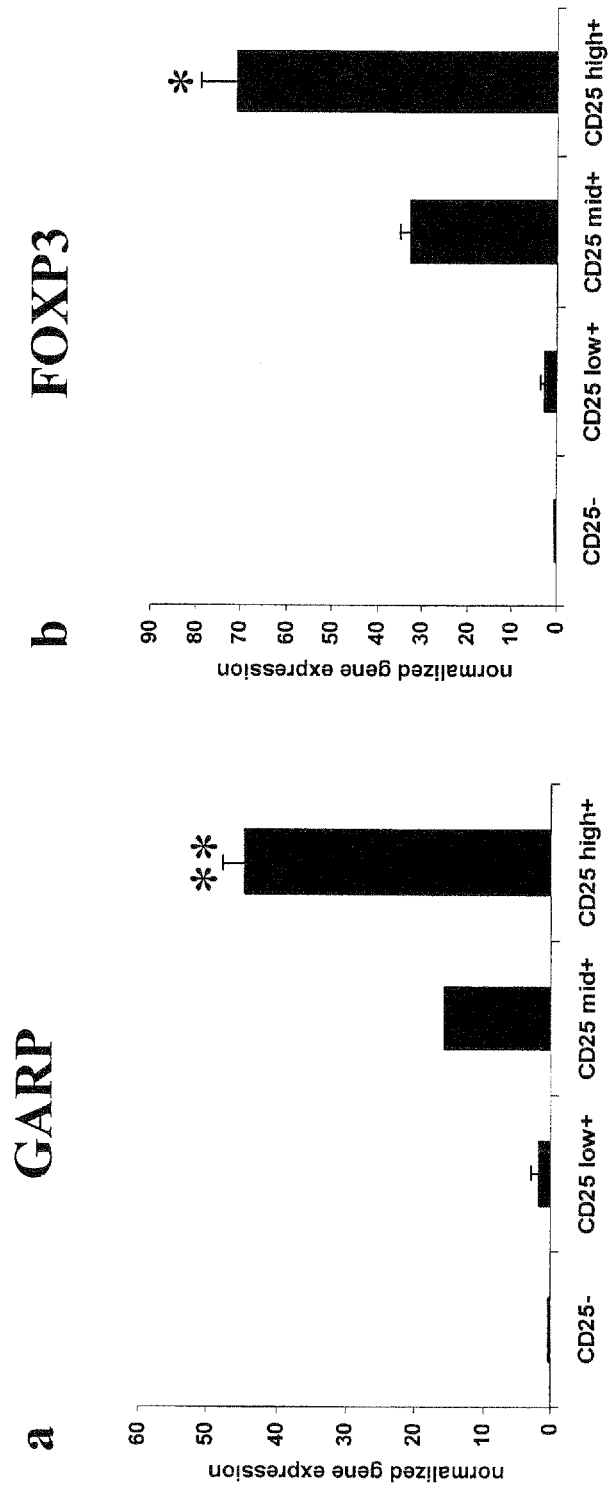
FIG. 3 illustrates an example of CD25high+Treg cells expressing stable and high levels of GARP mRNA. 18SrRNA-Normalized GARP (FIG. 3A) and FOXP3 (FIG. 3B) mRNA expression was measured by quantitative RT-PCR. Data summarizes four independent experiments. Results are expressed as the mean±SEM. *p=0.01 compared to CD25mid+ cells, **p=0.005 compared to CD25mid+ cells.

The data showed that, although plate bound anti-CD3 alone did not activate GARP or FOXP3, soluble anti-CD28 co-stimulation caused a slight increase of both GARP and FOXP3 expressions in CD25high+ cells (p>0.05). However, both GARP and FOXP3 genes were highly activated after administration of exogenous IL-2. In the presence of IL-2, the level of GARP mRNA was more upregulated (9.7±0.82 fold) than FOXP3 mRNA (2.8±0.19 fold) compared to the nonactivated CD25high+ cells (p=0.01, n=3) (FIG. 3b). Thus, GARP may be a more sensitive marker of IL-2 dependent stimulation of CD25high+ Treg cells than FOXP3.

Example 6

IL-2 Upregulation of GARP and FOXP3 in CD25mid+ Cells

It was asked whether or not CD25mid+ cells also modulated Treg cell markers in the presence of exogenous IL-2. CD25mid+, CD25low+ and CD25− cells were activated for 72 hours with immobilized anti-CD3 (0.5 µg/ml) in the presence of exogenous IL-2 (50 U/ml) and assessed for the mRNA expression of GARP (FIG. 5A) and FOXP3 (FIG. 5B) by Q-RT-PCR. Results from three separate donors are shown as the mean±SEM.

Compared to CD25high+ cells, the nonactivated CD25mid+ cells expressed significantly lower levels of GARP and FOXP3 mRNAs. However, these cells also showed upregulation of both GARP (FIG. 5A) and FOXP3 (FIG. 5B) transcription in anti-CD3+IL-2 stimulated conditions. These results indicated that the CD25mid+ cell population expresses lower, but significant amounts of GARP and FOXP3 mRNA in the unstimulated state than CD25high+ cells. Furthermore, similar to CD25high+ cells, GARP is a marker of exogenous IL-2 stimulation in the CD25mid+ T cell population.

Figure 5:
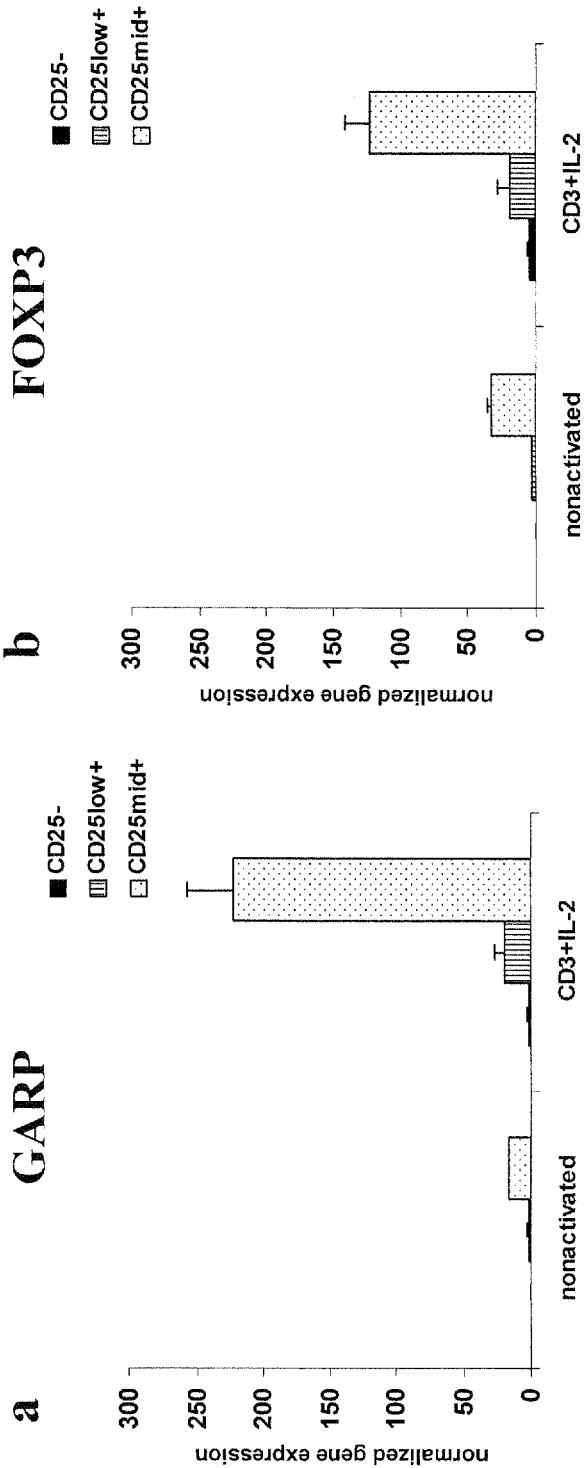
FIG. 5 shows an example of IL-2 dependent upregulation of GARP and FOXP3 in CD25mid+ cells. CD25mid+, CD25low+ and CD25− cells were activated for 72 hours with immobilized anti-CD3 (0.5 µg/ml) in the presence of exogenous IL-2 (50 U/ml) and assessed for the mRNA expression of GARP (FIG. 5A) and FOXP3 (FIG. 5B) by Q-RT-PCR. Results from three separate donors are shown as the mean±SEM.

Additionally, the IL-2 dependent stimulation of the CD25low+ population caused only a slight increase in the expression levels of GARP and FOXP3 mRNAs. Nonactivated CD25– cells expressed detectable levels of both GARP and FOXP3 mRNAs, but failed to increase GARP and FOXP3 transcription upon polyclonal stimulation (FIG. 5).

Example 7

Figure 6:
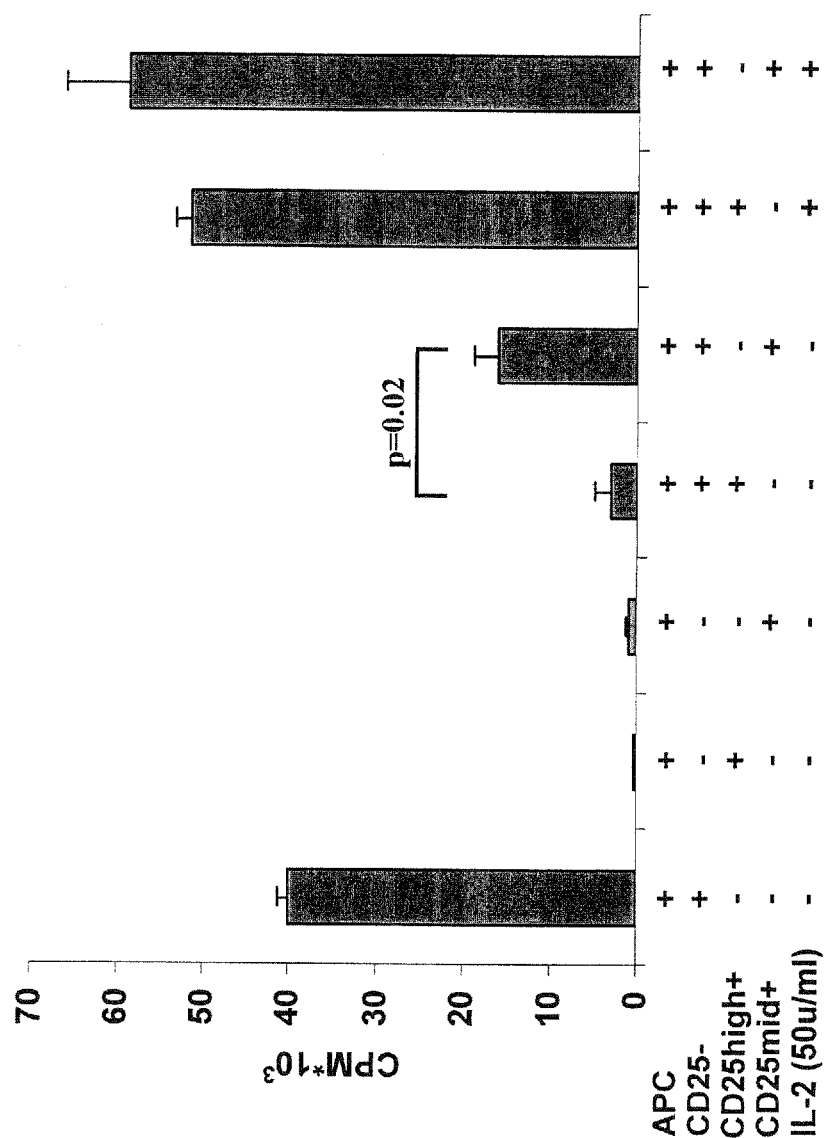
FIG. 6 shows an example of CD25+ high and mid cells suppressing the proliferative response of CD25− cells in co-culture.

CD25high+ T Cells Suppress the Proliferative Response of CD25– Cells Upon Co-Culture CD25high+, CD25mid+, CD25low+ and CD25– T cells were simultaneously isolated by high-speed flow cytometric sorting. To test the regulatory function of suppressor subsets, CD25high+ or CD25mid+ T cells were stimulated alone (15×$10^3$ cells/well) or co-cultured at a 1:1 ratio with autologous CD4+CD25– cells for 6 days with 100×$10^3$ irradiated (4000 rad) allogeneic APCs in the presence or absence of exogenous IL-2 (50 U/ml). Cells were pulsed with [$^3$H]-thymidine for additional 16 hours before harvesting. Summary of results from three separate donors is shown as the mean±SEM in FIG. 6.

CD25– T cells proliferated upon alloantigenic stimulation, yet neither CD25high+ nor CD25mid+ T cells proliferated in response to alloantigens. The CD25high+ Treg cells consistently suppressed the proliferation of responder cells (p=0.0001, n=3), and this suppression was reversible by the addition of exogenous IL-2 (50 U/ml). CD25mid+ cells also consistently suppressed CD25– responder T cell proliferation (p=0.005, n=3), but compared to CD25high+ T cells, the inhibitory capacity of CD25mid+ cells was lower (p=0.02, n=3). Human CD25low+ T cells, did not exhibit detectable regulatory function in vitro (data not shown).

Example 8

CD25mid+ T Cells Suppress More Consistently the IL-2 mRNA Production of CD25– Cells Upon Co-Culture than CD25high+ T Cells CD4+CD25+ regulatory T cells is known to suppress the expression of IL-2 mRNA in CD25– cells upon co-culture and this suppression is generally not abrogated in the presence of exogenous IL-2 in mice. In this study, it was examined whether human CD25high+ and CD25mid+ T cells inhibit the production of IL-2 in CD25– cells in the presence or absence of exogenous IL-2. To examine whether CD25high+ and CD25mid+ cells inhibit the production of IL-2 in CD25– cells, CD25high+ or CD25mid+ T cells were stimulated alone (20×$10^3$ cells/well) or co-cultured at a 1:1 ratio with autologous CD4+CD25– cells with 100×$10^3$ irradiated allogeneic APCs in the presence or absence of exogenous IL-2 (50 U/ml). Cells were harvested and total RNA was extracted after 5 days. Each Q-RT-PCR reaction was performed in triplicate using primers specific for IL-2 and 18S ribosomal RNA. 18SrRNA-normalized IL-2 expressions are shown from three independent experiments.

Figure 7:
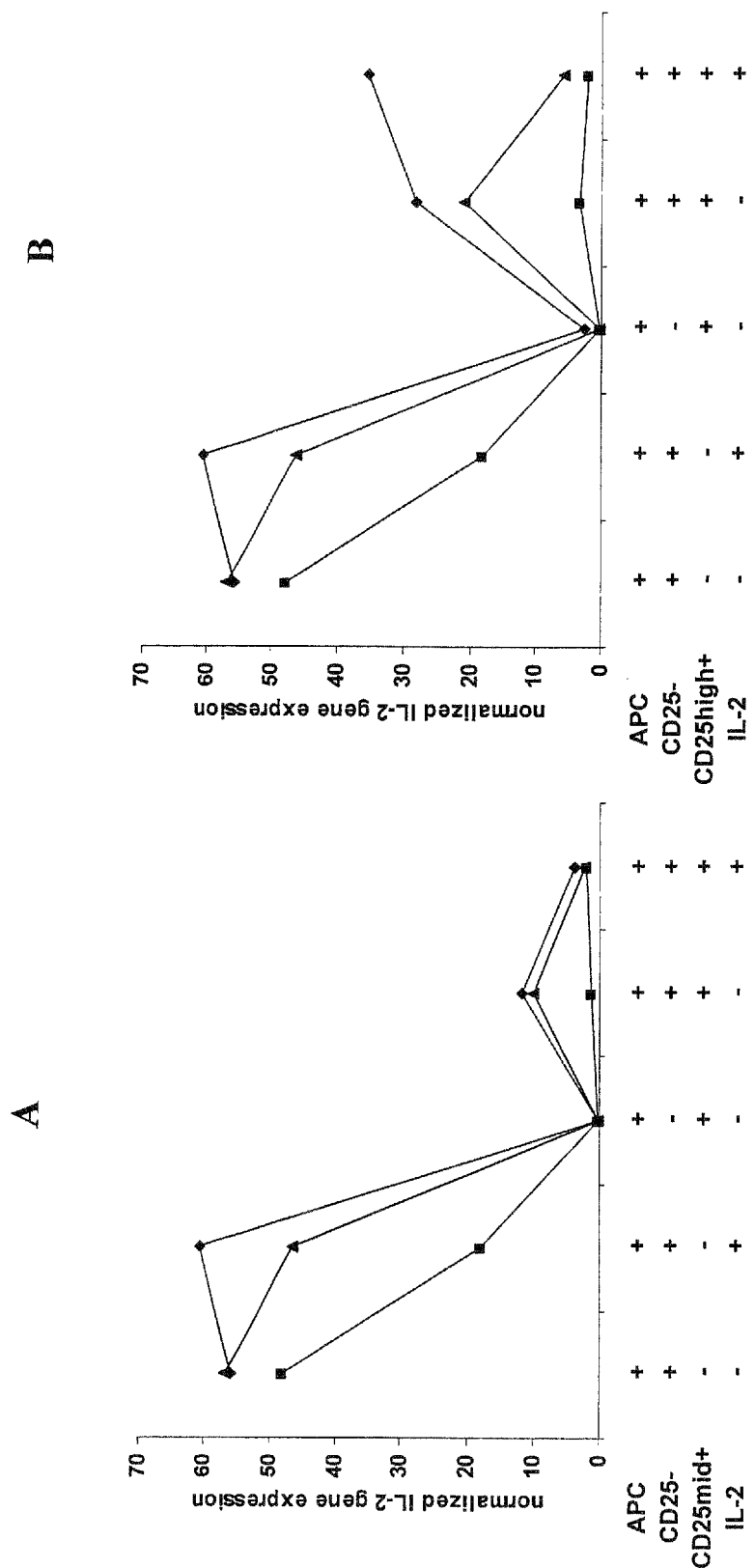
FIG. 7 shows an example of CD25mid+ cells (FIG. 7A) and CD25high+ cells (FIG. 7B) suppressing the IL-2 mRNA production of CD25− cells upon co-culture.

The results (FIG. 7) indicated that neither CD25high+ nor CD25mid cells expressed IL-2 mRNA alone upon stimulation. In co-culture, CD25mid+ cells (FIG. 7A) exhibited more consistent suppression of IL-2 mRNA production by CD25– cells compared to CD25high+ cells (FIG. 7B). Furthermore, the expression of IL-2 mRNA remained suppressed even in the presence of exogenous IL-2. These results showed that CD25mid+ cells, derived from normal human blood, represent a functional regulatory T cell population.

Example 9

CD25mid+ T Cells Proliferate after Appropriate Polyclonal Stimulation Whereas CD25high+ Cells Remain Anergic The anergic state of the CD25high+ and CD25mid+ Treg cells was tested. CD25high+CD25mid+, CD25low+ and CD25– cells were simultaneously sorted from normal human peripheral blood and stimulated alone (15×$10^3$ cells/well) with plate-bound anti-CD3 (0.54 ml), in the presence or absence of soluble anti-CD28 (1 μg/ml) and/or IL-2 (50 U/ml). Proliferation was determined by [$^3$H]-thymidine incorporation after 72 hours. Data are the summary of four independent experiments. Results are expressed as the mean±SEM. *p<0.05 compared with CD25– cells, **p<0.01 compared with CD25–cells.

Figure 8:
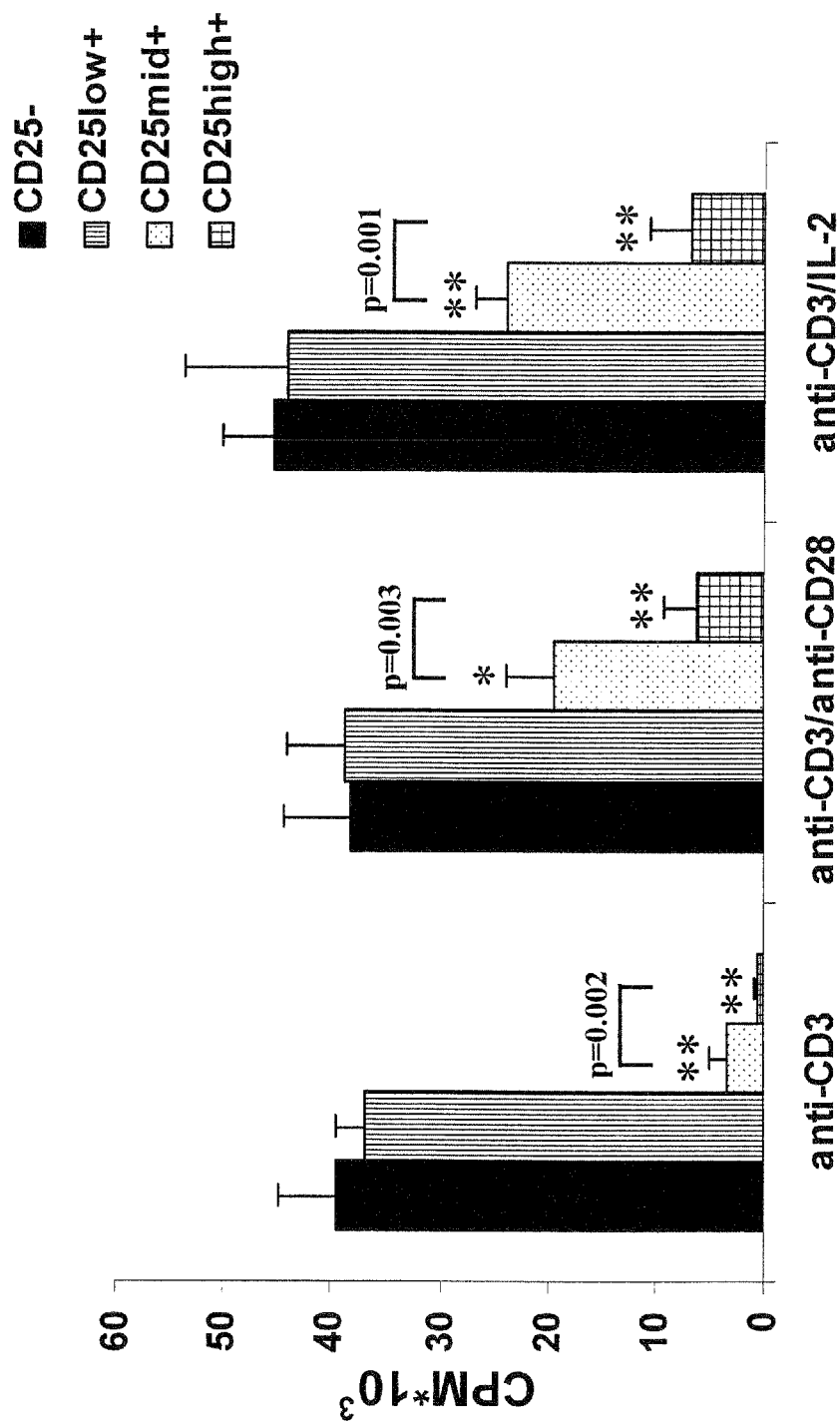
FIG. 8 shows an example of CD25mid+ cells proliferating after appropriate polyclonal stimulation whereas CD25high+ cells remain anergic.

The results (FIG. 8) showed that the CD25high+ cells did not proliferate after polyclonal stimulation, and underwent a slight proliferation in the presence of anti-CD28 (1 μg/ml) or exogenous IL-2 (50 U/ml). The proliferation of CD25– and CD25low+ cells was equally high after stimulation by anti-CD3, anti-CD3+anti-CD28 and anti-CD3+IL-2. Although the proliferation of CD25mid+ cells was significantly lower than CD25– and CD25low+, CD25mid+ proliferation was significantly higher than CD25high+ cells after polyclonal stimulation with anti-CD28 or exogenous IL-2 (p=0.03 and p=0.001, respectively). These results showed that CD25high+ cells are anergic, whereas CD25mid+ cells are capable of proliferating and consequently can be expanded in vitro with optimal polyclonal stimulation.

Example 10

Neither CD25high+ Nor CD25mid+Cells Express Cytokines Upon Polyclonal Stimulation CD25high+ regulatory T cells inhibit the proliferation of CD25–cells in a cytokine independent manner in vitro. Expression levels of IL-10 (FIG. 9A) and IL-2 (FIG. 9B) mRNAs were examined upon polyclonal activation using quantitative real time PCR. CD25high+CD25mid+, CD25low+ and CD25– cells were stimulated alone with immobilized anti-CD3 (0.5 μg/ml), in the presence or absence of soluble anti-CD28 (1 μg/ml) and/or IL-2 (50 U/ml) for 72 hours. Total RNA was extracted, reverse transcribed and cDNA was amplified in the presence of specific primers for IL-10 (FIG. 9A), IL-2 (FIG. 9B) or 18S. Each Q-RT-PCR reaction was performed in triplicate and the data are summaries of three independent experiments. The results are expressed as the mean±SEM The results (FIG. 9) show that, after 72 hours, the level of IL-10 mRNA expression was not detectable in CD25high+ and CD25mid+ cells with anti-CD3 stimulation. Upon additional stimulation with either anti-CD28 or IL-2, CD25high+ and CD25mid+ T cells expressed low (detectable) levels of IL-10 mRNAs. Similarly, the level of IL-2 mRNA in CD25high+ and CD25mid+ cells was only detectable after polyclonal stimulation with anti-CD28 and IL-2.

In contrast, activated CD25low+ cells expressed high levels of IL-10 and moderate levels of IL-2 mRNAs. These results indicate that, upon stimulation, CD25low+ cells are responsible for the production of IL-10, indicating that contamination of CD25low+ cells in either the CD25high+ or CD25mid+ cell population would result in IL-10 production without efficient suppressor function in these regulatory cell populations. Activated CD25− cells predominantly produced high levels of IL-2 and moderate levels of IL-10 mRNAs.

Example 11

Figure 10:
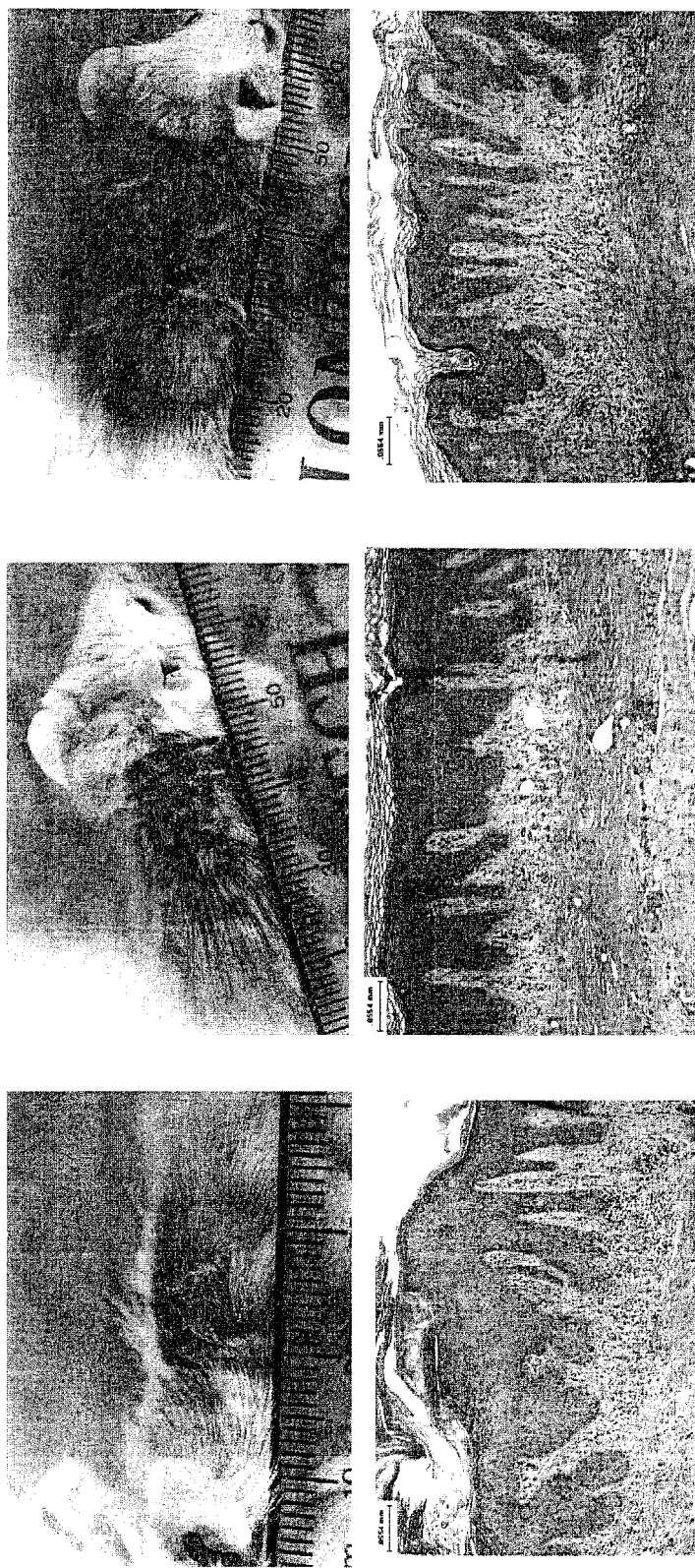
FIG. 10 shows example photographs of human skin engrafted onto SCID mice and then treated with PBS (control), intracutaneously-injected with Treg cells, or treated with cyclosporin.
Figure 11:
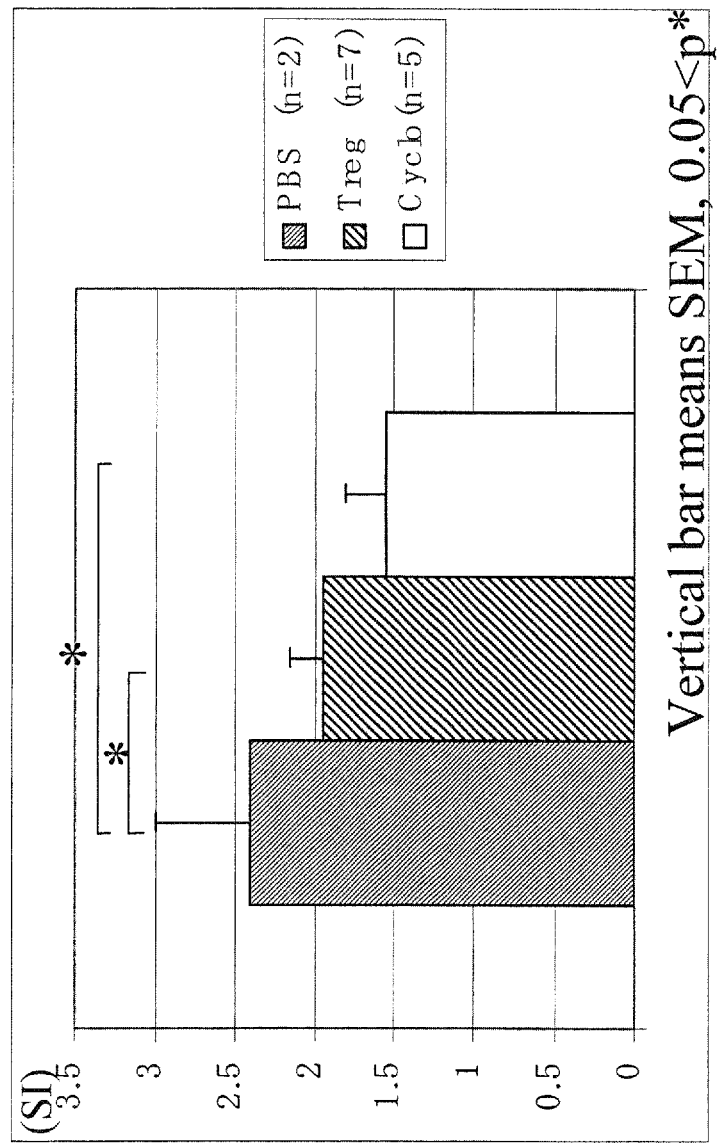
FIG. 11 shows example severity index (SI) measurements of the engrafted human skin from the mice described in the Brief Description of FIG. 10.
Figure 12:
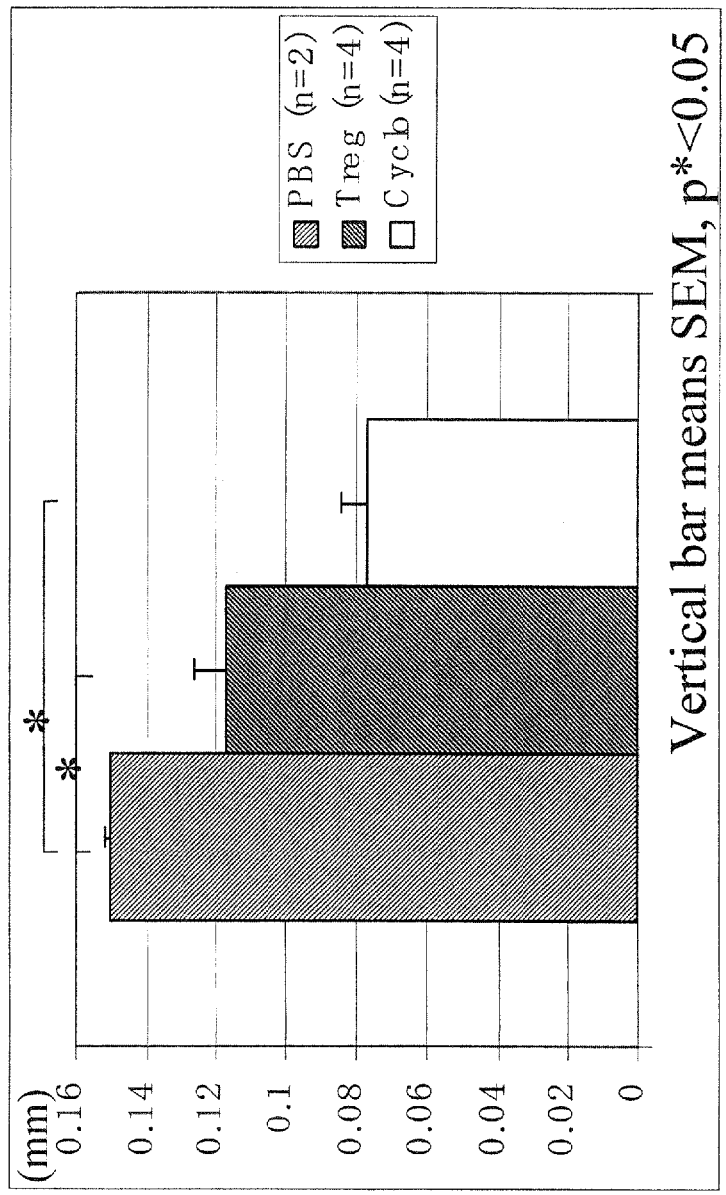
FIG. 12 shows example epidermal thickness measurements of the engrafted human skin from the mice described in the Brief Description of FIG. 10.

Treg Cells Administered to SCID Mice with a Human Skin Engraftment Reverse a Psoriatic Phenotype Human skin was grafted onto a SCID mouse. Untreated, the skin displayed a psoriatic phenotype (FIG. 10, PBS Treatment). Administration of Treg cells to the SCID mice by injection into the engrafted human skin indicated that the psoriatic phenotype was reversed (FIG. 10, Treg intracutaneous) to a comparable level as that when the SCID mice were treated with the immunosuppressive agent, cyclosporin (FIG. 10, Cyclosporin A treatment). Additional analysis of the engrafted skin of the SCID mice showed that the severity index (SI) for the skin in mice where Treg cells were injected intracutaneously was decreased compared to the skin in mice given PBS treatment, and not decreased to the level of the skin in mice given cyclosporin treatment (FIG. 11). Additional analysis of the engrafted skin of the SCID mice showed that epidermal thickness for the skin in the mice where Treg cells were injected intracutaneously was decreased compared to the skin in mice given PBS treatment, and not decreased to the level of the skin in mice given cyclosporin treatment (FIG. 12).

Example 12

Expression of Muring GARP Following Activation

Figure 13:
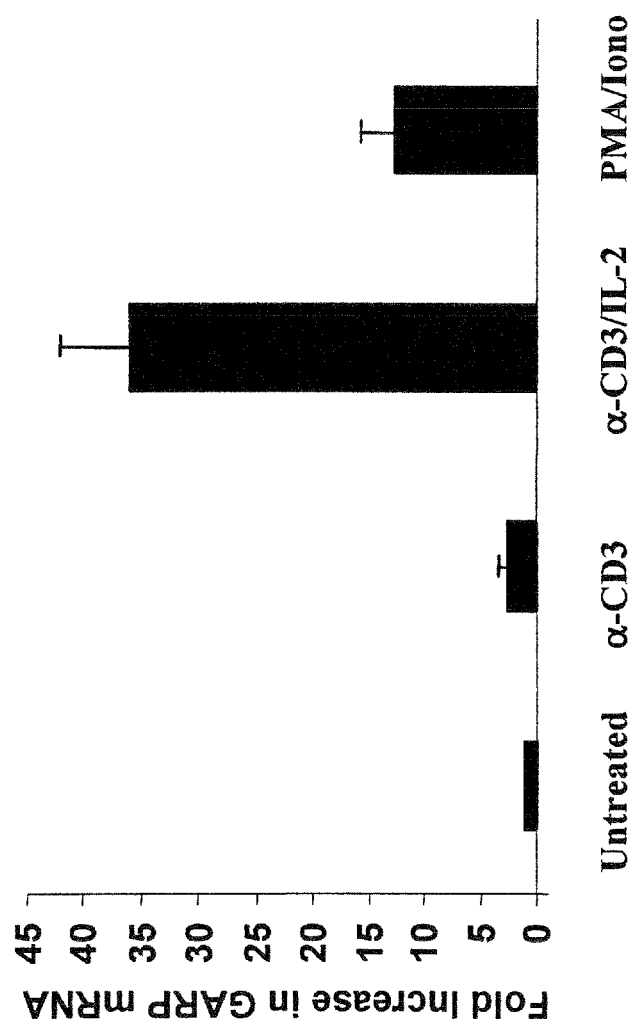
FIG. 13 shows the increase in murine GARP expression in the presence and absence of anti-CD3 (mouse specific), anti-CD3 and IL-2, phorbol myristate actetate (PMA)/Ionomycin or unstimulated.

Previous studies have demonstrated that mice also express the messenger RNA for GARP. In order to determine if mice also exhibit GARP mRNA expression, cells were extracted from murine thymus and lymph nodes, combined and then stimulated with either immobilized anti-mouseCD3 (0.25 μg/ml), in the presence or absence of soluble recombinant mIL-2 (50 U/ml), or the phorbol ester PMA (2.5 ng/ml) in the presence of ionomycin (1.0 μmol/L) for 18-24 h. Untreated cultured cells were used as control. Total RNA was extracted using a Qiagen midi-RNA kit, reverse transcribed and cDNA was amplified in the presence of specific primers for mGARP and m18S ribosomal RNA. We designed several primer/probe combinations specific for the published murine GARP sequence (XM_485967, gi:51761724) using the Applied Biosystems Primer Express software. Each Q-RT-PCR reaction was performed in triplicate, data are a summary of three independent experiments. Results are expressed as the mean±SEM. GARP mRNA upregulation was elicited by anti-CD3, PMA/Ionomycin and anti-CD3/IL-2 in increasing concentrations, respectively. The combination of anti-CD3/L-2 was nearly 3 fold greater than that elicited by phorbol ester treatment and nearly 10-fold greater than anti-CD3 treatment alone. FIG. 13 demonstrates the fold increase in mGARP calculated using Taqman PCR and −2 ΔΔCT values, normalized to untreated samples and standardized by m18S ribosomal RNA. Interestingly, the murine GARP primer pair used to successfully amplify the signal of mGARP following stimulation is specific to the amino terminus, as is the human primer pair produced by Applied Biosystems. Both human and mouse probes and primers are specific to the coding region for the signal peptide of the molecule.

While example compositions, methods, and so on have been illustrated by description, and while the descriptions are in considerable detail, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the invention is not limited to the specific details, the representative apparatus, and illustrative examples shown and described. Thus, this application is intended to embrace alterations, modifications, and variations that fall within the scope of the application. Furthermore, the preceding description is not meant to limit the scope of the invention. Rather, the scope of the invention is to be determined by the appended claims and their equivalents.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

We claim:

1. A method for screening cells for identity as regulatory T cells, the method comprising:
   providing a blood sample from a subject; and
   determining the amount of regulatory T cells in a specified volume of blood by identifying T cells in at least a portion of the blood sample that express glycoprotein A repetitions predominant (GARP) protein on the surface of the cells;
   wherein the cells expressing a GARP protein on the surface are identified by reacting with an antibody raised against at least a portion of the GARP protein.

2. The method of claim 1, wherein the antibody raised against at least a portion of the GARP protein is raised against at least a portion of the GARP protein having the amino acid sequence of SEQ. ID. NO. 1.

3. The method of claim 2, wherein the at least a portion of the GARP protein having the amino acid sequence of SEQ. ID. NO. 1 is selected from the group consisting of:
   amino acids 8-31 of SEQ. ID. NO. 1;
   amino acids 48-71 of SEQ. ID. NO. 1;
   amino acids 72-95 of SEQ. ID. NO. 1;
   amino acids 97-122 of SEQ. ID. NO. 1;
   amino acids 123-147 of SEQ. ID. NO. 1;
   amino acids 148-171 of SEQ. ID. NO. 1;
   amino acids 172-195 of SEQ. ID. NO. 1;
   amino acids 197-217 of SEQ. ID. NO. 1;
   amino acids 218-240 of SEQ. ID. NO. 1;
   amino acids 242-264 of SEQ. ID. NO. 1;
   amino acids 265-286 of SEQ. ID. NO. 1;
   amino acids 314-337 of SEQ. ID. NO. 1;
   amino acids 339-361 of SEQ. ID. NO. 1;
   amino acids 362-385 of SEQ. ID. NO. 1;
   amino acids 386-409 of SEQ. ID. NO. 1;
   amino acids 410-432 of SEQ. ID. NO. 1;
   amino acids 442-465 of SEQ. ID. NO. 1;
   amino acids 467-488 of SEQ. ID. NO. 1;
   amino acids 490-512 of SEQ. ID. NO. 1;
   amino acids 514-538 of SEQ. ID. NO. 1;
   amino acids 540-558 of SEQ. ID. NO. 1;
   amino acids 560-583 of SEQ. ID. NO. 1;
   and combinations thereof.

4. The method of claim 3, additionally comprising the step of isolating identified regulatory T cells from other cells.

5. The method of claim 4, wherein the antibody raised against at least a portion of the GARP protein is fluorescently labeled.

6. The method of claim 5, wherein the step of isolating identified regulatory T cells from other cells comprises flow sorting the regulatory T cells according to fluorescence of the regulatory T cells.

7. The method of claim 1, additionally comprising the step of isolating identified regulatory T cells from other cells.

8. The method of claim 7, wherein the antibody raised against at least a portion of the GARP protein is fluorescently labeled.

9. The method of claim 8, wherein the step of isolating identified regulatory T cells from other cells comprises flow sorting the regulatory T cells according to fluorescence of the regulatory T cells.

10. The method of claim 2, additionally comprising the step of isolating identified regulatory T cells from other cells.

11. The method of claim 10, wherein the antibody raised against at least a portion of the GARP protein is fluorescently labeled.

12. The method of claim 11, wherein the step of isolating identified regulatory T cells from other cells comprises flow sorting the regulatory T cells according to fluorescence of the regulatory T cells.

13. The method of claim 1, wherein the antibody raised against at least a portion of the GARP protein is fluorescently labeled.

14. The method of claim 13, wherein the step of isolating identified regulatory T cells from other cells comprises flow sorting the regulatory T cells according to fluorescence of the regulatory T cells.

15. The method of claim 2, wherein the antibody raised against at least a portion of the GARP protein is fluorescently labeled.

16. The method of claim 15, wherein the step of isolating identified regulatory T cells from other cells comprises flow sorting the regulatory T cells according to fluorescence of the regulatory T cells.

* * * * *

UNITED STATES PATENT AND TRADEMARK OFFICE
CERTIFICATE OF CORRECTION

| | | |
|---|---|---|
| PATENT NO. | : 8,815,526 B2 | Page 1 of 1 |
| APPLICATION NO. | : 11/910442 | |
| DATED | : August 26, 2014 | |
| INVENTOR(S) | : Garaczi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1564 days.

Signed and Sealed this
Twenty-third Day of February, 2016

Michelle K. Lee
*Director of the United States Patent and Trademark Office*

SEQUENCE LISTING

```
<160> NUMBER OF SEQ ID NOS: 24

<210> SEQ ID NO 1
<211> LENGTH: 662
<212> TYPE: PRT
<213> ORGANISM: Homo sapiens

<400> SEQUENCE: 1

Met Arg Pro Gln Ile Leu Leu Leu Leu Ala Leu Leu Thr Leu Gly Leu
1               5                   10                  15

Ala Ala Gln His Gln Asp Lys Val Pro Cys Lys Met Val Asp Lys Lys
```

```
            20                  25                  30
Val Ser Cys Gln Val Leu Gly Leu Leu Gln Val Pro Ser Val Leu Pro
            35                  40                  45

Pro Asp Thr Glu Thr Leu Asp Leu Ser Gly Asn Gln Leu Arg Ser Ile
 50                  55                  60

Leu Ala Ser Pro Leu Gly Phe Tyr Thr Ala Leu Arg His Leu Asp Leu
 65                  70                  75                  80

Ser Thr Asn Glu Ile Ser Phe Leu Gln Pro Gly Ala Phe Gln Ala Leu
                 85                  90                  95

Thr His Leu Glu His Leu Ser Leu Ala His Asn Arg Leu Ala Met Ala
            100                 105                 110

Thr Ala Leu Ser Ala Gly Gly Leu Gly Pro Leu Pro Arg Val Thr Ser
            115                 120                 125

Leu Asp Leu Ser Gly Asn Ser Leu Tyr Ser Gly Leu Leu Glu Arg Leu
            130                 135                 140

Leu Gly Glu Ala Pro Ser Leu His Thr Leu Ser Leu Ala Glu Asn Ser
145                 150                 155                 160

Leu Thr Arg Leu Thr Arg His Thr Phe Arg Asp Met Pro Ala Leu Glu
                165                 170                 175

Gln Leu Asp Leu His Ser Asn Val Leu Met Asp Ile Glu Asp Gly Ala
            180                 185                 190

Phe Glu Gly Leu Pro Arg Leu Thr His Leu Asn Leu Ser Arg Asn Ser
            195                 200                 205

Leu Thr Cys Ile Ser Asp Phe Ser Leu Gln Gln Leu Arg Val Leu Asp
            210                 215                 220

Leu Ser Cys Asn Ser Ile Glu Ala Phe Gln Thr Ala Ser Gln Pro Gln
225                 230                 235                 240

Ala Glu Phe Gln Leu Thr Trp Leu Asp Leu Arg Glu Asn Lys Leu Leu
                245                 250                 255

His Phe Pro Asp Leu Ala Ala Leu Pro Arg Leu Ile Tyr Leu Asn Leu
            260                 265                 270

Ser Asn Asn Leu Ile Arg Leu Pro Thr Gly Pro Pro Gln Asp Ser Lys
            275                 280                 285

Gly Ile His Ala Pro Ser Glu Gly Trp Ser Ala Leu Pro Leu Ser Ala
            290                 295                 300

Pro Ser Gly Asn Ala Ser Gly Arg Pro Leu Ser Gln Leu Leu Asn Leu
305                 310                 315                 320

Asp Leu Ser Tyr Asn Glu Ile Glu Leu Ile Pro Asp Ser Phe Leu Glu
                325                 330                 335

His Leu Thr Ser Leu Cys Phe Leu Asn Leu Ser Arg Asn Cys Leu Arg
            340                 345                 350

Thr Phe Glu Ala Arg Arg Leu Gly Ser Leu Pro Cys Leu Met Leu Leu
            355                 360                 365

Asp Leu Ser His Asn Ala Leu Glu Thr Leu Glu Leu Gly Ala Arg Ala
            370                 375                 380

Leu Gly Ser Leu Arg Thr Leu Leu Leu Gln Gly Asn Ala Leu Arg Asp
385                 390                 395                 400

Leu Pro Pro Tyr Thr Phe Ala Asn Leu Ala Ser Leu Gln Arg Leu Asn
                405                 410                 415

Leu Gln Gly Asn Arg Val Ser Pro Cys Gly Gly Pro Asp Glu Pro Gly
            420                 425                 430

Pro Ser Gly Cys Val Ala Phe Ser Gly Ile Thr Ser Leu Arg Ser Leu
            435                 440                 445
```

```
Ser Leu Val Asp Asn Glu Ile Glu Leu Leu Arg Ala Gly Ala Phe Leu
    450                 455                 460

His Thr Pro Leu Thr Glu Leu Asp Leu Ser Ser Asn Pro Gly Leu Glu
465                 470                 475                 480

Val Ala Thr Gly Ala Leu Gly Gly Leu Glu Ala Ser Leu Glu Val Leu
                485                 490                 495

Ala Leu Gln Gly Asn Gly Leu Met Val Leu Gln Val Asp Leu Pro Cys
            500                 505                 510

Phe Ile Cys Leu Lys Arg Leu Asn Leu Ala Glu Asn Arg Leu Ser His
        515                 520                 525

Leu Pro Ala Trp Thr Gln Ala Val Ser Leu Glu Val Leu Asp Leu Arg
    530                 535                 540

Asn Asn Ser Phe Ser Leu Leu Pro Gly Ser Ala Met Gly Gly Leu Glu
545                 550                 555                 560

Thr Ser Leu Arg Arg Leu Tyr Leu Gln Gly Asn Pro Leu Ser Cys Cys
                565                 570                 575

Gly Asn Gly Trp Leu Ala Ala Gln Leu His Gln Gly Arg Val Asp Val
            580                 585                 590

Asp Ala Thr Gln Asp Leu Ile Cys Arg Phe Ser Ser Gln Glu Val
        595                 600                 605

Ser Leu Ser His Val Arg Pro Glu Asp Cys Glu Lys Gly Gly Leu Lys
    610                 615                 620

Asn Ile Asn Leu Ile Ile Leu Thr Phe Ile Leu Val Ser Ala Ile
625                 630                 635                 640

Leu Leu Thr Thr Leu Ala Ala Cys Cys Val Arg Arg Gln Lys Phe
                645                 650                 655

Asn Gln Gln Tyr Lys Ala
            660

<210> SEQ ID NO 2
<211> LENGTH: 4163
<212> TYPE: DNA
<213> ORGANISM: Homo sapiens

<400> SEQUENCE: 2
ttgatttggt atagtgggaa catttgcttt ggagacagat gaactggatt ctgatcgtga     60
ccctgctatt ttctccttgt gtgactttgg agccatgaga ccccagatcc tgctgctcct    120
ggccctgctg acctaggcc tggctgcaca acaccaagac aaagtgccct gtaagatggt    180
ggacaagaag gtctcgtgcc aggttctggg cctgctccag gtcccctcgg tgctcccgcc    240
agacactgag acccttgatc tatctgggaa ccagctgcgg agtatcctgg cctcacccct    300
gggcttctac acggcacttc gtcacctgga cctgagcacc aatgagatca gcttcctcca    360
gccaggagcc ttccaggccc tgacccacct ggagcacctc agcctggctc acaaccggct    420
ggcgatggcc actgcgctga gtgctggtgg cctgggcccc tgccacgcg tgacctccct    480 ggacctgtct gggaacagcc tgtacagcgg cctgctggag cggctgctgg gggaggcacc    540
cagcctgcat accctctcac tggcggagaa cagtctgact cgcctcaccc gccacacctt    600
ccgggacatg cctgcgctgg agcagcttga cctgcatagc aacgtgctga tggacatcga    660
ggatggcgcc ttcgagggcc tgccccgcct gacccatctc aacctctcca ggaattccct    720
cacctgcatc tccgacttca gcctccagca gctgcgggtg ctagacctga gctgcaacag    780
catcgaggcc tttcagacgg cctcccagcc ccaggctgag ttccagctca cctggcttga    840
```

```
cctgcgggag aacaaactgc tccatttccc cgacctggcc gcgctcccga gactcatcta    900
cctgaacttg tccaacaacc tcatccggct ccccacaggg ccaccccagg acagcaaggg    960
catccacgca ccttccgagg gctggtcagc cctgcccctc tcagccccca gcgggaatgc   1020
cagcggccgc ccccttttccc agctcttgaa tctggatttg agctacaatg agattgagct   1080
catccccgac agctttcttg agcacctgac ctccctgtgc ttcctgaacc tcagcagaaa   1140
ctgcttgcgg acctttgagg cccggcgctt aggctccctg ccctgcctga tgctccttga   1200
cttaagccac aatgccctgg agacactgga actgggcgcc agagccctgg ggtctctgcg   1260
gacgctgctc ctacagggca atgccctgcg ggacctgccc ccatacacct ttgccaatct   1320
ggccagcctg cagcggctca acctgcaggg gaaccgagtc agccctgtg gggggccaga   1380
tgagcctggc ccctccggct gtgtggcctt ctccggcatc acctccctcc gcagcctgag   1440
cctggtggat aatgagatag agctgctcag ggcaggggcc ttcctccaca ccccactgac   1500
tgagctggac ctttcttcca atcctgggct ggaggtggcc acgggggcct tgggaggcct   1560
ggaggcctcc ttggaggtcc tggcactgca gggcaacggg ctgatggtcc tgcaggtgga   1620
cctgccctgc ttcatctgcc tcaagcggct caatcttgcc gagaaccgcc tgagccacct   1680
tcccgcctga cacaggctg tgtcactgga ggtgctggac ctgcgaaaca acagcttcag   1740
cctcctgcca ggcagtgcca tgggtggcct ggagaccagc ctccggcgcc tctacctgca   1800
ggggaatcca ctcagctgct gcggcaatgg ctggctggca gcccagctgc accagggccg   1860
tgtggacgtg gacgccaccc aggacctgat ctgccgcttc agctcccagg aggaggtgtc   1920
cctgagccac gtgcgtcccg aggactgtga aaggggggga ctgaagaaca tcaacctcat   1980
catcatcctc accttcatac tggtctctgc catcctcctc accacgctgg ccgcctgctg   2040
ctgcgtccgc cggcagaagt ttaaccaaca gtataaagcc taaagaagcc gggagacact   2100
ctaggtcagt gggggagcct gaggtacaga aagagtgag gactgactca aggtcacaca   2160
gtgatccgga tccagaaact ctggtctcca aattacagcc caggacacct ttctctgccg   2220
cctgctgcat cagtgggtga cccccttccc gggctgcact ttgggtccag ctgtggaagc   2280
cagaagttgg gcggtttcag ggacagccga gaataatgtt gacctgtcag atcaacaaat   2340
cttcactgag catgtatttt gtgccacacc ctgctctggg cactgggaat gctgggaaat   2400
gagatacatt cccgccctca gaatctccc agtctggtag agagagtgc tgcagagcca   2460
cgtggccgcc acgcagtgtg cttagggcct gaggtgtgaa agcccagggc tccagagctc   2520
ggcaggcccc gctggtttgg tgcggtgagt cctgccccgg ctgtgcaggg tgagggaggg   2580
ccaagccagg aggatttgtc tgagacattt ccaagcagac tgtttgtcac gtcttctgag   2640
aatgactttc agtctctctg aaaatgaaaa gcttaggacc ggaagagaga attggagctg   2700
tacgagtgtg tctcggatct ggtattgtta ggtgggccac ggcggctcca gcagggtctg   2760
gttaaggggt ccagcccagc actgaccat tccgtctcct gctctggact tgccctctcc   2820
cttcctggca ctctcatgtt gcatacccctg accccagtgc tgctctaagc accgtccctg   2880
cccagcccca cttctccatc gcagccccac cttggctgct gagccaggag ctaaaacctt   2940
agatatctgg ttctgttttg cacccagctt ggcagatgtg gatttgaatc caagccttgt   3000
gtctgcccct atgtgacagc tctatatttt atcccgtttt tataaaagag gaaactgaag   3060
ttctgaaaat ctccttccag ggccccagct aactaatgcc ataggtgaga ttcaaacctt   3120
catccttctg tctccagggc ctgatctta ccactgcagg ggctgcaggc cgttaagtgg   3180
acaggaagtg gccccacata gcccgagcag ggtctggaag catcctgtgc tgtgcacacc   3240
```

-continued

```
tgctctctcc tctctcccag gcaggcagct gcaggcgctc tcctccttct ctgcctgttt    3300
ccctcctccc ttcctttcca ccctggtgtg ggttctcctg ttctctctgt gctcttgcat    3360
tctctcattc ccttttcctc tatggagcag agcctggagt ttgagactat ggaatccaac    3420
ctccccattg cacagatggg gaaactgagg cttaggaaga gaatgaaact tgtggagagc    3480
ttatacagaa cctctggggg aaaaaagagc ccttatttgt ggggtgagat tgggggttgg    3540
accagagtga tgtcctctct cagctatcac atcacaagat aatgctggct ccaaacttcc    3600
tttctgtgcc tcatcatgca aggatctttt tccctctta caaaaacagg taaaaagcct     3660
cacccagatg accccatcc ctcataccat ggagtcatga gctgtctggg aagaatggac     3720
gtgctgggac caactcaaga ccttgttttg ctgtcttcat catcttacct gtgcttggcc    3780
cacagtctgg ctcatgatgt gggctcagta atgtgcgaga agtgaaaat gccactctct     3840
ccacccatt ttacagagga gaacaccaag gcccagagga agttaaggga gagtcaatgg     3900
gcagagccag ggctaggccc tggtggtgtg tggagcaccc aggcagaccc agtcctggtt    3960
gggatcacac ccacgggtgc tactgcacgt aacactcctc cttaggcctg gaggccaagg    4020
tgtgggtccc cacgcctgat cttgaaaac actacacagg gctgctgtca cttcccaggg    4080
cccaggcctc agcccaggcc tcgggaccaa ctctttgtat aacctacctg aatgtattaa    4140
aaactaattt tggaaaaaaa aaa                                            4163
```

<210> SEQ ID NO 3
<211> LENGTH: 24
<212> TYPE: PRT
<213> ORGANISM: Homo sapiens

<400> SEQUENCE: 3

Leu Leu Ala Leu Leu Thr Leu Gly Leu Ala Ala Gln His Gln Asp Lys
1               5                   10                  15

Val Pro Cys Lys Met Val Asp Lys
            20

<210> SEQ ID NO 4
<211> LENGTH: 24
<212> TYPE: PRT
<213> ORGANISM: Homo sapiens

<400> SEQUENCE: 4

Pro Pro Asp Thr Glu Thr Leu Asp Leu Ser Gly Asn Gln Leu Arg Ser
1               5                   10                  15

Ile Leu Ala Ser Pro Leu Gly Phe
            20

<210> SEQ ID NO 5
<211> LENGTH: 24
<212> TYPE: PRT
<213> ORGANISM: Homo sapiens

<400> SEQUENCE: 5

Tyr Thr Ala Leu Arg His Leu Asp Leu Ser Thr Asn Glu Ile Ser Phe
1               5                   10                  15

Leu Gln Pro Gly Ala Phe Gln Ala
            20

<210> SEQ ID NO 6
<211> LENGTH: 26
<212> TYPE: PRT

<213> ORGANISM: Homo sapiens

<400> SEQUENCE: 6

Thr His Leu Glu His Leu Ser Leu Ala His Asn Arg Leu Ala Met Ala
1               5                   10                  15

Thr Ala Leu Ser Ala Gly Gly Leu Gly Pro
            20                  25

<210> SEQ ID NO 7
<211> LENGTH: 25
<212> TYPE: PRT
<213> ORGANISM: Homo sapiens

<400> SEQUENCE: 7

Leu Pro Arg Val Thr Ser Leu Asp Leu Ser Gly Asn Ser Leu Tyr Ser
1               5                   10                  15

Gly Leu Leu Glu Arg Leu Leu Gly Glu
            20                  25

<210> SEQ ID NO 8
<211> LENGTH: 24
<212> TYPE: PRT
<213> ORGANISM: Homo sapiens

<400> SEQUENCE: 8

Ala Pro Ser Leu His Thr Leu Ser Leu Ala Glu Asn Ser Leu Thr Arg
1               5                   10                  15

Leu Thr Arg His Thr Phe Arg Asp
            20

<210> SEQ ID NO 9
<211> LENGTH: 24
<212> TYPE: PRT
<213> ORGANISM: Homo sapiens

<400> SEQUENCE: 9

Met Pro Ala Leu Glu Gln Leu Asp Leu His Ser Asn Val Leu Met Asp
1               5                   10                  15

Ile Glu Asp Gly Ala Phe Glu Gly
            20

<210> SEQ ID NO 10
<211> LENGTH: 21
<212> TYPE: PRT
<213> ORGANISM: Homo sapiens

<400> SEQUENCE: 10

Pro Arg Leu Thr His Leu Asn Leu Ser Arg Asn Ser Leu Thr Cys Ile
1               5                   10                  15

Ser Asp Phe Ser Leu
            20

<210> SEQ ID NO 11
<211> LENGTH: 23
<212> TYPE: PRT
<213> ORGANISM: Homo sapiens

<400> SEQUENCE: 11

Gln Gln Leu Arg Val Leu Asp Leu Ser Cys Asn Ser Ile Glu Ala Phe
1               5                   10                  15

Gln Thr Ala Ser Gln Pro Gln
            20

<210> SEQ ID NO 12
<211> LENGTH: 23
<212> TYPE: PRT
<213> ORGANISM: Homo sapiens

<400> SEQUENCE: 12

Glu Phe Gln Leu Thr Trp Leu Asp Leu Arg Glu Asn Lys Leu Leu His
1               5                   10                  15

Phe Pro Asp Leu Ala Ala Leu
            20

<210> SEQ ID NO 13
<211> LENGTH: 22
<212> TYPE: PRT
<213> ORGANISM: Homo sapiens

<400> SEQUENCE: 13

Pro Arg Leu Ile Tyr Leu Asn Leu Ser Asn Asn Leu Ile Arg Leu Pro
1               5                   10                  15

Thr Gly Pro Pro Gln Asp
            20

<210> SEQ ID NO 14
<211> LENGTH: 24
<212> TYPE: PRT
<213> ORGANISM: Homo sapiens

<400> SEQUENCE: 14

Leu Ser Gln Leu Leu Asn Leu Asp Leu Ser Tyr Asn Glu Ile Glu Leu
1               5                   10                  15

Ile Pro Asp Ser Phe Leu Glu His
            20

<210> SEQ ID NO 15
<211> LENGTH: 23
<212> TYPE: PRT
<213> ORGANISM: Homo sapiens

<400> SEQUENCE: 15

Thr Ser Leu Cys Phe Leu Asn Leu Ser Arg Asn Cys Leu Arg Thr Phe
1               5                   10                  15

Glu Ala Arg Arg Leu Gly Ser
            20

<210> SEQ ID NO 16
<211> LENGTH: 24
<212> TYPE: PRT
<213> ORGANISM: Homo sapiens

<400> SEQUENCE: 16

Leu Pro Cys Leu Met Leu Leu Asp Leu Ser His Asn Ala Leu Glu Thr
1               5                   10                  15

Leu Glu Leu Gly Ala Arg Ala Leu
            20

<210> SEQ ID NO 17
<211> LENGTH: 23
<212> TYPE: PRT
<213> ORGANISM: Homo sapiens

<400> SEQUENCE: 17

```
Gly Ser Leu Arg Thr Leu Leu Leu Gln Gly Asn Ala Leu Arg Asp Leu
1               5                   10                  15

Pro Pro Tyr Thr Phe Ala Asn
            20
```

<210> SEQ ID NO 18
<211> LENGTH: 23
<212> TYPE: PRT
<213> ORGANISM: Homo sapiens

<400> SEQUENCE: 18

```
Ala Ser Leu Gln Arg Leu Asn Leu Gln Gly Asn Arg Val Ser Pro Cys
1               5                   10                  15

Gly Gly Pro Asp Glu Pro Gly
            20
```

<210> SEQ ID NO 19
<211> LENGTH: 24
<212> TYPE: PRT
<213> ORGANISM: Homo sapiens

<400> SEQUENCE: 19

```
Ile Thr Ser Leu Arg Ser Leu Ser Leu Val Asp Asn Glu Ile Glu Leu
1               5                   10                  15

Leu Arg Ala Gly Ala Phe Leu His
            20
```

<210> SEQ ID NO 20
<211> LENGTH: 22
<212> TYPE: PRT
<213> ORGANISM: Homo sapiens

<400> SEQUENCE: 20

```
Pro Leu Thr Glu Leu Asp Leu Ser Ser Asn Pro Gly Leu Glu Val Ala
1               5                   10                  15

Thr Gly Ala Leu Gly Gly
            20
```

<210> SEQ ID NO 21
<211> LENGTH: 24
<212> TYPE: PRT
<213> ORGANISM: Homo sapiens

<400> SEQUENCE: 21

```
Glu Ala Ser Leu Glu Val Leu Ala Leu Gln Gly Asn Gly Leu Met Val
1               5                   10                  15

Leu Gln Val Asp Leu Pro Cys Phe
            20
```

<210> SEQ ID NO 22
<211> LENGTH: 25
<212> TYPE: PRT
<213> ORGANISM: Homo sapiens

<400> SEQUENCE: 22

```
Ile Cys Leu Lys Arg Leu Asn Leu Ala Glu Asn Arg Leu Ser His Leu
1               5                   10                  15

Pro Ala Trp Thr Gln Ala Val Ser Leu
            20                  25
```

<210> SEQ ID NO 23
<211> LENGTH: 19

```
<212> TYPE: PRT
<213> ORGANISM: Homo sapiens

<400> SEQUENCE: 23

Val Leu Asp Leu Arg Asn Asn Ser Phe Ser Leu Leu Pro Gly Ser Ala
1               5                   10                  15

Met Gly Gly

<210> SEQ ID NO 24
<211> LENGTH: 24
<212> TYPE: PRT
<213> ORGANISM: Homo sapiens

<400> SEQUENCE: 24

Glu Thr Ser Leu Arg Arg Leu Tyr Leu Gln Gly Asn Pro Leu Ser Cys
1               5                   10                  15

Cys Gly Asn Gly Trp Leu Ala Ala
            20
```